(12) United States Patent
Bloembergen et al.

(10) Patent No.: US 11,369,570 B2
(45) Date of Patent: Jun. 28, 2022

(54) APTAMER BIOCONJUGATE DRUG DELIVERY DEVICE

(71) Applicant: ECOSYNTHETIX LTD., Lansing, MI (US)

(72) Inventors: Steven Bloembergen, Okemos, MI (US); Ian J. McLennan, Burlington (CA); Nathan Jones, Hamilton (CA); Areet Krsna Ganesh Shermon, Waterloo (CA); Abdel Elsayed, Waterloo (CA); Juewen Liu, Kitchener (CA)

(73) Assignee: GREENMARK BIOMEDICAL INC., Lansing, MI (US)

( * ) Notice: Subject to any disclaimer, the term of this patent is extended or adjusted under 35 U.S.C. 154(b) by 256 days.

(21) Appl. No.: 14/360,503

(22) PCT Filed: Sep. 21, 2012

(86) PCT No.: PCT/US2012/056582
§ 371 (c)(1),
(2) Date: May 23, 2014

(87) PCT Pub. No.: WO2013/081720
PCT Pub. Date: Jun. 6, 2013

(65) Prior Publication Data
US 2015/0025029 A1    Jan. 22, 2015

Related U.S. Application Data

(63) Continuation of application No. 13/310,287, filed on Dec. 2, 2011, now abandoned.

(60) Provisional application No. 61/653,636, filed on May 31, 2012, provisional application No. 61/565,313, filed on Nov. 30, 2011, provisional application No. 61/419,106, filed on Dec. 2, 2010.

(30) Foreign Application Priority Data

Dec. 2, 2011 (WO) ................ PCT/US2011/063102

(51) Int. Cl.
| | |
|---|---|
| A61K 9/26 | (2006.01) |
| A61K 9/14 | (2006.01) |
| A61K 9/51 | (2006.01) |
| B82Y 5/00 | (2011.01) |
| A61K 9/16 | (2006.01) |
| C08B 31/18 | (2006.01) |
| C08B 33/00 | (2006.01) |
| C08B 35/00 | (2006.01) |
| A61K 47/54 | (2017.01) |
| A61K 47/69 | (2017.01) |
| C08B 31/00 | (2006.01) |
| A61K 31/704 | (2006.01) |
| A61K 47/36 | (2006.01) |

(52) U.S. Cl.
CPC ............ *A61K 9/145* (2013.01); *A61K 9/1676* (2013.01); *A61K 9/5161* (2013.01); *A61K 31/704* (2013.01); *A61K 47/549* (2017.08); *A61K 47/6939* (2017.08); *B82Y 5/00* (2013.01); *C08B 31/003* (2013.01); *C08B 31/185* (2013.01); *C08B 33/00* (2013.01); *C08B 35/00* (2013.01); *A61K 47/36* (2013.01); *Y10S 977/773* (2013.01); *Y10S 977/906* (2013.01); *Y10T 428/2982* (2015.01)

(58) Field of Classification Search
CPC .... A61K 9/145; A61K 9/1676; A61K 9/5161; A61K 31/704; A61K 47/36; A61K 47/549; A61K 47/6939
See application file for complete search history.

(56) References Cited

U.S. PATENT DOCUMENTS

| | | | |
|---|---|---|---|
| 2,148,951 | A | 2/1939 | Maxwell |
| 2,328,537 | A | 9/1943 | Felton |
| 2,500,950 | A | 3/1950 | Konigsberg |
| 2,801,242 | A | 7/1957 | Kerr et al. |
| 2,819,240 | A | 1/1958 | De et al. |
| 2,929,811 | A | 3/1960 | Hofreiter et al. |
| 2,989,521 | A | 6/1961 | Kenti et al. |
| 4,126,669 | A | 11/1978 | Rothman et al. |
| 5,087,649 | A | 2/1992 | Wegner et al. |
| 6,011,092 | A | 1/2000 | Seppala et al. |
| 6,340,527 | B1 | 1/2002 | Van Soest et al. |
| 6,379,494 | B1 | 4/2002 | Jewel et al. |

(Continued)

FOREIGN PATENT DOCUMENTS

| | | |
|---|---|---|
| EP | 0311873 | 4/1989 |
| EP | 1961769 A1 | 8/2008 |

(Continued)

OTHER PUBLICATIONS

Xiao et al. Chinese Science Bulletin. 2006; 51(14): 1693-1697.*

(Continued)

*Primary Examiner* — David Browe

(57) ABSTRACT

A delivery device for a active agent comprises nanoparticles based on a biopolymer such as starch. The delivery device may also be in the form of an aptamer-biopolymer-active agent conjugate wherein the aptamer targets the device for the treatment of specific disorders, such as cancer. The delivery device survives for a period of time in the body sufficient to allow for transport and uptake of the delivery device into targeted cells. The degree of crosslinking can provide a desired release profile of the active agent at, near or inside the target cells. The nanoparticles may be made by applying a high shear force in the presence of a cross linker. The particles may be predominantly in the range of 50-150 nm and form a colloidal dispersion of crosslinked hydrogel particles in water.

10 Claims, 11 Drawing Sheets

Specification includes a Sequence Listing.

(56) References Cited

U.S. PATENT DOCUMENTS

| | | | |
|---|---|---|---|
| 6,677,386 | B1* | 1/2004 | Giezen .................... C08B 30/12 |
| | | | 106/206.1 |
| 6,749,868 | B1 | 6/2004 | Desai et al. |
| 6,755,915 | B1 | 6/2004 | Van Soest et al. |
| 6,825,252 | B2 | 11/2004 | Helbling et al. |
| 6,921,430 | B2 | 7/2005 | Bloembergen et al. |
| 7,550,441 | B2 | 6/2009 | Farokhzad et al. |
| 8,043,480 | B2 | 10/2011 | Lahann et al. |
| 8,048,453 | B1 | 11/2011 | Sung et al. |
| 8,759,322 | B2 | 6/2014 | Akiyoshi et al. |
| 9,133,279 | B2 | 9/2015 | Perrier et al. |
| 10,285,943 | B2 | 5/2019 | Bloembergen et al. |
| 2002/0136769 | A1 | 9/2002 | Kabanov et al. |
| 2003/0219785 | A1 | 11/2003 | Hallahan et al. |
| 2004/0028745 | A1 | 2/2004 | Bouhadir et al. |
| 2004/0126900 | A1 | 7/2004 | Barry et al. |
| 2004/0241382 | A1 | 12/2004 | Bloembergen et al. |
| 2005/0191359 | A1 | 9/2005 | Goldshtein et al. |
| 2006/0002852 | A1 | 1/2006 | Saltzman et al. |
| 2006/0292280 | A1* | 12/2006 | Soper et al. .................. 426/534 |
| 2007/0224280 | A1 | 9/2007 | Lillard et al. |
| 2008/0081074 | A1 | 4/2008 | Gu et al. |
| 2008/0233200 | A1 | 9/2008 | Sung et al. |
| 2008/0241257 | A1 | 10/2008 | Popescu et al. |
| 2009/0061010 | A1 | 3/2009 | Zale et al. |
| 2009/0117549 | A1 | 5/2009 | Tan et al. |
| 2009/0155409 | A1 | 6/2009 | Sexton et al. |
| 2009/0196831 | A1 | 8/2009 | Yang et al. |
| 2009/0226521 | A1 | 9/2009 | Smyth et al. |
| 2009/0312402 | A1 | 12/2009 | Contag et al. |
| 2010/0093659 | A1 | 4/2010 | Natunen et al. |
| 2010/0093933 | A1 | 4/2010 | Karagianni et al. |
| 2010/0143738 | A1 | 6/2010 | Bloembergen et al. |
| 2010/0166872 | A1 | 7/2010 | Singh et al. |
| 2010/0266491 | A1 | 10/2010 | Farokhzad et al. |
| 2010/0267802 | A1 | 10/2010 | Sullenger |
| 2010/0272639 | A1 | 10/2010 | Dutcher et al. |
| 2011/0014296 | A1 | 1/2011 | Chen et al. |
| 2011/0038939 | A1 | 2/2011 | Lvov et al. |
| 2011/0042841 | A1 | 2/2011 | Wildi et al. |
| 2011/0212901 | A1 | 9/2011 | Kazunari et al. |
| 2011/0244044 | A1 | 10/2011 | Rossi et al. |
| 2011/0244048 | A1 | 10/2011 | Amiji et al. |
| 2012/0003888 | A1 | 1/2012 | Lee et al. |
| 2012/0141551 | A1 | 7/2012 | Bloembergen et al. |
| 2017/0112949 | A1 | 4/2017 | Lahann et al. |

FOREIGN PATENT DOCUMENTS

| | | |
|---|---|---|
| GB | 1420392 | 1/1976 |
| JP | 2002-544335 | 12/2002 |
| JP | 2004-500438 | 1/2004 |
| JP | 2005-535604 | 11/2005 |
| WO | 0040617 | 7/2000 |
| WO | 0066090 A1 | 11/2000 |
| WO | 0069916 A1 | 11/2000 |
| WO | 2001078786 | 10/2001 |
| WO | 03010206 A1 | 2/2003 |
| WO | 2003101425 | 12/2003 |
| WO | 2005108471 A1 | 11/2005 |
| WO | 2007069272 | 6/2007 |
| WO | 2008022127 A2 | 4/2008 |
| WO | 2008060575 A2 | 5/2008 |
| WO | 2009146147 A2 | 12/2009 |
| WO | 2010042823 | 4/2010 |
| WO | 2010053140 | 5/2010 |
| WO | 2010065750 A1 | 6/2010 |
| WO | 2010080557 | 7/2010 |
| WO | 2010084088 | 7/2010 |
| WO | 2011071742 A2 | 6/2011 |
| WO | 2011155979 A2 | 12/2011 |
| WO | 2012075414 | 6/2012 |
| WO | 2012162845 | 12/2012 |
| WO | 2013081720 A1 | 6/2013 |

OTHER PUBLICATIONS

Fishman et al. J Agric Food Chem. 1996; 44: 3182-3188.*
Aravind et al. Cancer Nano. 2012; 3: 1-12.*
Gu et al. Nanotoday. 2007; 2(3): 14-21. (Year: 2007).*
Jones, N., et al., "Targeted Starch Nanoparticles for Cancer Therapy", Design Symposium, Mar. 23, 2012.
Shin, J.Y., et al., "Rheological properties of starch latex dispersions and starch latex-containing coating colors", Presented at PaperCon 2012, "Growing the Future", New Orleans, LA, Apr. 21-25, 2012.
Bloembergen, S., et al., "Biolatex Binders for Paper and Paperboard Applications", Journal of Pulp and Paper Science, 2010, pp. 1-11, vol. 36, No. 3-4.
Lee, Do Ik, et al., "Development of New Biobased Emulsion Binders", PaperCon2010, Talent, Technology and Transformation, Atlanta, GA, May 2-5, 2010; 46 pages.
Jain, Akhlesh Kumar et al., Effective insulin delivery using starch nanoparticles as a potential trans-nasal mucoadhesive carrier, European Journal of Pharmaceutics 69 (2008) 426-435.
Saboktakin, Mohammad Reza et al. pH-sensitive starch hydrogels via free radical graft copolymerization, synthesis and properties, Carbohydrate Polymers 77 (2009) 634-638.
Simi, C.K., et al. Hydrophobic grafted and cross-linked starch nanoparticles for drug delivery, Bioprocess Biosyst Eng (2007) 30:173-180.
Song et al., "Starch nanoparticle formation via reactive extrusion and related mechanism study", Carbohydrate Polymers, 2011, vol. 85, pp. 208-214.
Bloembergen, S., et al., "Specialty Biobased Monomers and Emulsion Polymers Derived from Starch", PTS Advanced Coating Fundamentals Symposium, Munich, Germany, Oct. 11-14, 2010, pp. 1-19.
Soundararjan, Sridharan, et al., "Plasma Membrane Nucleolin is a Receptor for an Anticancer Aptamer AS1411 in MV4-11 Leukemia Cells", Molecular Pharmacology, 2009, pp. 984-991, vol. 76, No. 5.
Shangguan, D, "Aptamers Evolved from Cultured Cancer Cells Reveal Molecular Differences of Cancer Cells in Patient Samples", Clinical Chemistry, vol. 53, No. 6, pp. 1-3, 2007.
Ozalp, Veli Cengiz, et al., "Aptamer-Gated Nanoparticles for Smart Drug Delivery", Pharmaceuticals, 2011, vol. 4, pp. 1137-1157.
Saenger, W. V., "Cyclodextrin-Einschubverbindungen in Forschung ung Industrie", Angew. Chem., 1980, pp. 343-361, vol. 92.
Wenz, G., "Cyclodextrine als Bausteine supramolekularer Strukturen und Funktionseinten", Angew. Chem. 1994, vol. 106, pp. 851-870.
Bloembergen, et al., "Paper Binder Performance with Nanoparticle Biolatex™: EcoSynthetix develops EcoSphere® biolatex for replacement of petroleum based latex binders", ACFS, Montreal, Jun. 11-13, 2008.
Fishman et al., Molar masses and sizes of starches by high-performance size-exclusion chromatography with on-line multi-angle laser light scattering detection, J Agric. Food Chem. 1996. 44, pp. 3182-3188.
Herr, J.K., et al., "Aptamer-conjugated nanoparticles for selective collection and detection of cancer cells"., Anal. Chem., 2006, pp. 2918-2924, vol. 78, No. 9.
Bates, Paula J. et al., "Discovery and Development of the G-rich Oligonucleotide AS1411 as a Novel Treatment for Cancer", Experimental and Molecular Pathology, vol. 86, No. 3, pp. 151-164, Jun. 2009.
Peng, Xiang-Hong, et al., "Targeted magnetic iron oxide nanoparticles for tumor imaging and therapy", International Journal of Nanomedicine, 2008, pp. 311-321, vol. 3, No. 3.
Farokhzad, Omid C., et al., "Nanoparticle-Aptamer Bioconjugates: A new Approach for Targeting Prostate Cancer Cells", Cancer Research, vol. 64, pp. 7668-7672, Nov. 1, 2004.
International Search Report of PCT/US2012/056582, dated Feb. 28, 2013.
Davis, S.S., "Microspheres and Drug Therapy: Pharmaceutical, Immunological and Medical Aspects", Elsevier, New York, NY, USA, Chapter 2, 1984, pp. 25-37.
Lai, P.S., et al., "AS1411 aptamer-conjugated polymeric micelle for targetable cancer therapy", Nanotech Conference & Expo 2010, Jun. 21-24, 2010, Anaheim, CA, Abstract only.

(56) References Cited

OTHER PUBLICATIONS

Stuart, R.K., et al., "Randomized phase II trial of the nucleolin targeting aptamer AS1411 combined with high-dose cytarabine in relapsed/refractory acute myeloid leukemia (AML)", J. Clin. Oncol., 2009, vol. 27(15s), Abstract only.

Mongelard, F. and P. Bouvet, "AS-1411, a guanosine-rich oligonucleotide aptamer targeting nucleolin for the potential treatment of cancer, including acute myeloid leukemia", Curr. Opin. Mol. Ther., Feb. 2010; pp. 107-114, vol. 12(1), Abstract only.

International Search Report and Written Opinion issued in related International Application No. PCT/US2011/063102, dated Jul. 6, 2012.

Thiele, C. et al., "Nanoparticle of anionic starch and cationic cyclodextrin derivatives for the targeted delivery of drugs", Polym. Chem., 2011, vol. 2, pp. 209-215.

Barker, E.D., "The Synthesis and Characterization of a Novel Polysaccharide Hydrogel for Biomedical Applications Including the Treatment of Malignant Tumors and the Prevention of Metastatic Disease." Thesis, University of Tennessee at Knoxville, Aug. 2007, pp. i-viii and 1-142 (150 total sheets).

Hamidi, M. et al. "Hydrogel Nanoparticles in Drug Delivery." Advanced Drug Delivery Reviews, vol. 60, 2008, pp. 1638-1649.

Amin S et al. Hydrogels as Potential Drug Delivery Systems. Scientific Research and Essay. 2009; 3(11): 1175-1183.

Ma, X. et al., Fabrication and Characterization of Citric Acid-Modified Starch Nanoparticles/Plasticized-Starch Composites. Biomacromolecules, vol. 9, 2008, pp. 3314-3320.

Xiao et al. Preparation of folate-conjugated starch nanoparticles and its application to tumor-targeted drug delivery vector. Chinese Science Bulletin 2006; 51(14):1693-1697.

Wu, Yanrong et al., DNA aptamer-micelle as an efficient detection/delivery vehicle toward cancer cells, Proceedings of the National Academy of Sciences of the United States of America, vol. 107, No. 1 Jan. 5-10, 2010.

Shangguan, D. et al., Aptamers evolved from live cells as effective molecular probes for cancer study, Proc Natl Acad Sci U S A. Aug. 8, 2006;103(32):11838-43.

Blank, Michael et al., Systematic Evolution of a DNA Aptamer Binding to Rat Brain Tumor Microvessels. Selective Targeting of Endothelial Regulatory Protein Pigpen., J. Biol. Chem. 276 (2001) 16464-16468.

Office Action dated Jul. 5, 2012 in related U.S. Appl. No. 13/310,287.
Office Action dated Nov. 21, 2012 in related U.S. Appl. No. 13/310,287.
Office Action dated Jul. 18, 2013 in related U.S. Appl. No. 13/310,287.
Office Action dated Oct. 31, 2013 in related U.S. Appl. No. 13/310,287.
Office Action dated Apr. 3, 2014 in related U.S. Appl. No. 13/310,287.
Office Action dated Jun. 16, 2014 in related U.S. Appl. No. 13/310,287.
Office Action dated Jul. 21, 2014 in related U.S. Appl. No. 13/310,287.
Examiner's Answer to Appeal Brief dated Aug. 6, 2015 in related U.S. Appl. No. 13/310,287.
Office Action dated Feb. 7, 2013 in related U.S. Appl. No. 13/614,120.
Office Action dated Jul. 29, 2013 in related U.S. Appl. No. 13/614,120.
Office Action dated Apr. 4, 2014 in related U.S. Appl. No. 13/614,120.
Office Action dated Jun. 13, 2014 in related U.S. Appl. No. 13/614,120.
Office Action dated Jul. 24, 2014 in related U.S. Appl. No. 13/614,120.
Office Action dated Dec. 8, 2014 in related U.S. Appl. No. 13/614,120.
Office Action dated Mar. 20, 2014 in related U.S. Appl. No. 13/990,278.
Xiao, Suyao et al., Studies of poly-L-lysine-starch nanoparticle preparation and its application as gene carrier, Science in China Ser. B Chemistry 2005 vol. 48 No. 2 162-166.
Office Action dated Aug. 3, 2015 in related U.S. Appl. No. 13/990,278.
Office Action dated Oct. 9, 2015 in related U.S. Appl. No. 13/990,278.
Office Action dated May 5, 2016 in related U.S. Appl. No. 13/990,278.

Heidel, Jeremy D. et al. Cyclodextrin-Containing Polymers: Versatile Platforms of Drug Delivery Materials, Journal of Drug Delivery, vol. 2012.

Sasaki, Hiroshi et al., A combination of desmopressin and docetaxel inhibit cell proliferation and invasion mediated by urokinase-type plasminogen activator (uPA) in human prostate cancer cells, Biochemical and Biophysical Research Communications 464 (2015) 848-854.

Alonso, Daniel F. et al. Antimetastatic effect of desmopressin in a mouse mammary tumor model, Breast Cancer Research and Treatment 57: 271-275, 1999.

Canadian Patent Application No. 2,819,240, Examiner's Requisition dated Jan. 11, 2018.

Corre et al., "Starch Nanoparticles: A Review," Biomacromolecules, May 2010, vol. 11 (5), pp. 1139-1153.

European Patent Application No. 11845209, Extended European Search Report dated Mar. 7, 2017.

European Patent Application No. 11845209, Supplementary Partial European Search Report dated Jul. 29, 2016.

European Patent Application No. 11845209.3, Office Action dated Nov. 21, 2017.

Ex Parte Podack Patent Trial and Appeal Board Appeal No. 2014-006893, Nov. 14, 2016, pp. 1-14 and a title page (15 total sheets).

International Patent Application No. PCT/US2011/063102, International Preliminary Report on Patentability and Written Opinion dated Jun. 13, 2013.

International Patent Application No. PCT/US2012/056582, International Preliminary Report on Patentability and Written Opinion dated Jun. 12, 2014.

Soontornworajit et al., "Aptamer-Functionalized in Situ Injectable Hydrogel for Controlled Protein Release," Journal of Biomacromolecules, Sep. 1, 2010, vol. 11 (10), pp. 2724-2730.

U.S. Appl. No. 13/990,278, Final Office Action dated Jan. 22, 2018.
U.S. Appl. No. 13/990,278, Non-Final Office Action dated Jun. 14, 2017.
U.S. Appl. No. 13/990,278, Non-Final Office Action dated Nov. 23, 2016.
U.S. Appl. No. 13/990,278, Notice of Allowance dated Mar. 30, 2018.
U.S. Appl. No. 13/310,287, Decision on Appeal dated Mar. 31, 2017.

Written Opinion for Application No. PCT/US2011/063102, dated Jul. 6, 2012, 8 pages.
Written Opinion for Application No. PCT/US2012/056582, dated Feb. 28, 2013, 9 pages.

Alexiou et al., "Targeting Cancer Cells: Magnetic Nanoparticles as Drug Carriers," European Biophysics Journal, 2006, vol. 35(5), pp. 446-450.

Alzate P., et al., "Micro and Nanoparticles of Native and Modified Cassava Starches as Carriers of the Antimicrobial Potassium Sorbate," Starch, 2016, vol. 68(11-12), pp. 1038-1047.

Canadian Patent Application No. 2,790,763, Office Action dated Apr. 30, 2020.
Canadian Patent Application No. 2,790,763, Office Action dated Jan. 12, 2021.
Canadian Patent Application No. 2,790,763, Office Action dated Aug. 6, 2019.
Canadian Patent Application No. 2,819,240, Office Action dated Aug. 28, 2019.
Canadian Patent Application No. 2,819,240, Office Action dated May 8, 2020.
Canadian Patent Application No. 2,819,240, Office Action dated Sep. 26, 2018.

Dave et al., "Regenerable DNA-Functionalized Hydrogels for Ultrasensitive, Instrument-Free Mercury(II) Detection and Removal in Water," Journal of the American Chemical Society, Aug. 2010, vol. 132 (36), pp. 12668-12673.

El-Feky et al., "Utilization of Crosslinked Starch Nanoparticles as a Carrier for Indomethacin and Acyclovir Drugs," Journal of Nanomedicine & Nanotechnology, 2015, vol. 6(1); 1000254, pp. 1-8.

European Patent Application No. 11845209.3, Office Action dated Oct. 24, 2018.

(56) References Cited

OTHER PUBLICATIONS

Farokhzad et al., "Nanoparticle-Aptamer Bioconjugates for Cancer Targeting," Expert Opinion on Drug Delivery, May 2006, vol. 3 (3), pp. 311-324.

Kaptein S.J.F., et al., "A Derivate of the Antibiotic Doxorubicin Is a Selective Inhibitor ofDengue and Yellow Fever Virus Replication In Vitro," Antimicrobial Agents and Chemotherapy, 2010, vol. 54(12), pp. 5269-5280.

Kawano et al., "Effects of Polyethylene Glycol Spacer Length and Ligand Density on Folate Receptor Targeting of Liposomal Doxorubicin in Vitro," Journal of Drug Delivery, 2011, vol. 2011, Article ID 160967, 6 pages.

Lee et al., "Delivery of Liposomes Into Cultured KB Cells via Folate Receptor-Mediated Endocytosis," The Journal of Biological Chemistry, Feb. 1994, vol. 269 (5), pp. 3198-3204.

Mangalam et al., "Cellulose/DNA Hybrid Nanomaterials," Biomacromolecules, Mar. 2009, vol. 10 (3), pp. 497-504.

Milla et al., "PEGylation of Proteins and Liposomes: A Powerful and Flexible Strategy to Improve the Drug Delivery," Current Drug Metabolism, Jan. 2012, vol. 13 (1), pp. 105-119.

Moore M.D., et al., "Generation of neutralizing aptamers against herpes simplex virus type 2: potential components of multivalent microbicides," The Journal of general virology, 2011, pp. 1493-1499.

Nationwide Children's Hospital, Herpes Simplex Virus (HSV), Jun. 1993. pages 1-2.

Phillips et al., "Applications of Aptamers in Cancer Cell Biology," Analytica Chimica Acta, Jul. 2008, vol. 621 (2), pp. 101-108.

Rupendra Mukerjea, Giles Slocum and John F. Robyt. "Determination of the maximum water solubility of eight native starches andthe solubility of their acidic-methanol and -ethanol modified analogues." Carbohydrate Research, vol. 342 (2007) pp. 103-110. (Year: 2007).

Shangguan et al., "Aptamers Evolved From Live Cells as Effective Molecular Probes for Cancer Study," Proceedings of the National Academy of Sciences, Aug. 2006, vol. 103 (32), pp. 11838-11843.

Suk et al., "PEGylation as a Strategy for Improving Nanoparticle-Based Drug and Gene Delivery," Advanced Drug Delivery Reviews, Apr. 2016, vol. 99 (Pt A), pp. 28-51.

Thapa et al., "Folate-PEG Conjugates of a Far-Red Light-Activatable Paclitaxel Prodrug to Improve Selectivity Toward Folate Receptor-Positive Cancer Cells" ACS Omega, Oct. 2017, vol. 2(10), pp. 6349-6360.

U.S. Appl. No. 13/990,278, Non-Final Office Action dated Sep. 13, 2018.
U.S. Appl. No. 16/391,918, Restriction Requirement dated Mar. 20, 2020.
U.S. Appl. No. 16/383,998, Non-Final Office Action dated Jul. 2, 2020.
U.S. Appl. No. 16/383,998, Final Office Action dated Nov. 10, 2020.
U.S. Appl. No. 16/383,998, Non-Final Office Action dated Apr. 16, 2021.
U.S. Appl. No. 16/391,918, Non-Final Office Action dated Sep. 4, 2020.
U.S. Appl. No. 13/990,278, Non-Final Office Action dated Jul. 23, 2018.
U.S. Appl. No. 13/990,278, Notice of Allowance dated Jan. 15, 2019.
U.S. Appl. No. 16/383,998, Final Office Action dated Mar. 24, 2020.
Wang et al., "Superparamagnetic Iron Oxide Nanoparticle-Aptamer Bioconjugates for Combined Prostate Cancer Imaging andTherapy." ChemMedChem, vol. 3, 2008, pp. 1311-1315.
Yamada et al., "Design of Folate-Linked Liposomal Doxorubicin to Its Antitumor Effect in Mice," Clinical Cancer Research, Dec. 2008, vol. 14 (24), pp. 8161-8168.
Yang et al., "Investigation of Folate-Conjugated Fluorescent Silica Nanoparticles for Targeting Delivery to Folate Receptor-Positive Tumors and Their Internalization Mechanism," International Journal of Nanomedicine, 2011, vol. 6, pp. 2023-2032.
Canadian Patent Application No. 2,790,763, Office Action dated Jul. 23, 2021.
U.S. Appl. No. 16/391,918, Final Office Action dated Jun. 29, 2021.
European Patent Application No. 19774807.2, Extended European Search Report dated Oct. 28, 2021.
Shi et al., "Preparation of Starch-based Nanoparticles Through High-pressure Homogenization and Miniemulsion Cross-linking: Influence of Various Process Parameters on Particle Size and Stability," Carbohydrate Polymers, Feb. 1, 2011, vol. 83, pp. 1604-1610.
U.S. Appl. No. 16/383,998, Non-Final Office Action dated Oct. 25, 2021.
Canadian Patent Application No. 2,790,763, Office Action dated Sep. 25, 2018.
Canadian Patent Application No. 2,790,763, Office Action dated Feb. 21, 2022.

* cited by examiner

Native Starch Granules

EcoSphere® 2202

D10 = 70 nm
D50 = 117 nm
D90 = 206 nm

Structure of a Carboxylated SB Latex Particle

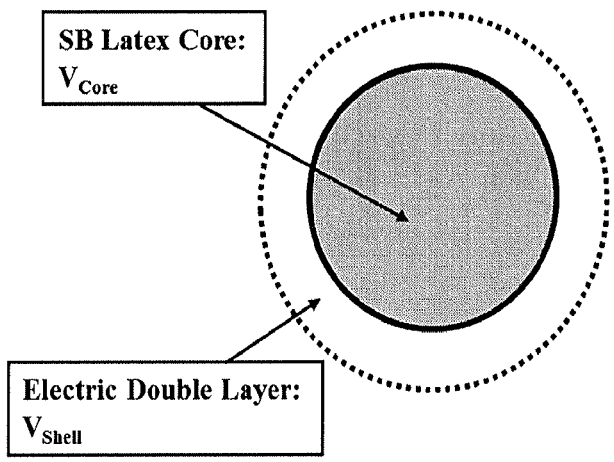

- SB Latex Core: $V_{Core}$
- Electric Double Layer: $V_{Shell}$

Since SB Latex particle cores are not swollen, the swell ratio is one:

$$V_{Core\text{-}swollen} / V_{Core\text{-}unswollen} = 1.0$$

FIGURE 6A

Structure of a Water-Swollen, Crosslinked Starch Nanoparticle

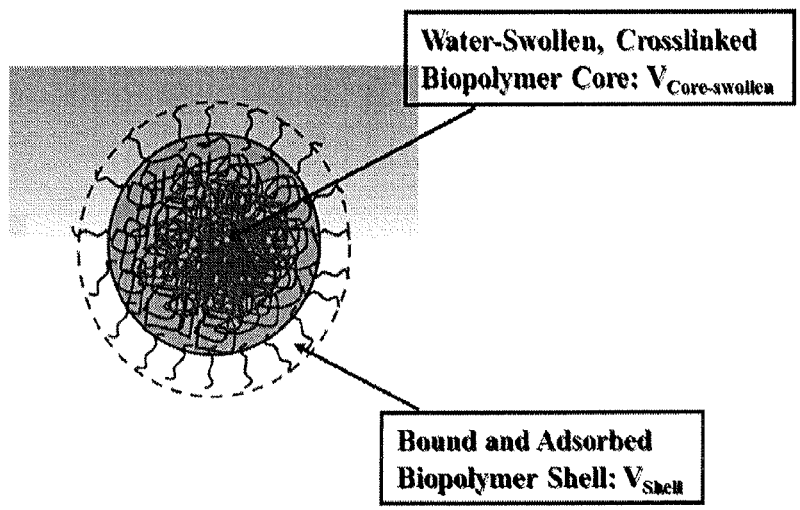

- Water-Swollen, Crosslinked Biopolymer Core: $V_{Core\text{-}swollen}$
- Bound and Adsorbed Biopolymer Shell: $V_{Shell}$ If $V_{Shell}$ is assumed to be 2 times $V_{Core\text{-}unswollen}$, then the swell ratio will become (at extreme dilution):

$$V_{Core\text{-}swollen} / V_{Core\text{-}unswollen} = 4.7$$

At 40% solids this swell ratio is:

$$V_{Core\text{-}swollen} / V_{Core\text{-}unswollen} = 2.5$$

FIGURE 6B

APTAMER BIOCONJUGATE DRUG DELIVERY DEVICE

CROSS-REFERENCES TO RELATED APPLICATIONS

This application is a National Stage Entry of International Application No. PCT/US2012/056582, filed on Sep. 21, 2012 which claims the benefit of International application number PCT/US2011/063102 filed on Dec. 2, 2011; U.S. patent application Ser. No. 13/310,287 filed on Dec. 2, 2011; US provisional patent application No. 61/653,636 filed on May 31, 2012 and 61/656,313 filed on Jun. 6, 2012. International Application No. PCT/US2012/056582, filed on Sep. 21, 2012; International application number PCT/US2011/063102 filed on Dec. 2, 2011; U.S. patent application Ser. No. 13/310,287 filed on Dec. 2, 2011; US provisional patent application No. 61/653,636 filed on May 31, 2012 and 61/656,313 filed on Jun. 6, 2012 incorporated by reference.

FIELD

This specification relates to a delivery device for drugs or other agents, to methods of making and using the delivery device, and to the treatment of cancer.

BACKGROUND

The following discussion is not an admission that anything described below is common general knowledge.

U.S. Pat. No. 6,340,527 to Van Soest et al. describes microparticles having a particle size of 50 nm to 1 mm consisting of a chemically crosslinked starch shell containing an active ingredient. The particles are obtained by first preparing an oil in water emulsion of the active ingredient in a hydrophobic phase and starch, or a dispersion of a solid active ingredient and starch in water. The active ingredient may be a medicament which is released in the digestive tract when the starch degrades.

US Patent Application Publication US 2008/0241257 to Popescu et al. describes a nanoparticle of a biodegradable polymer containing a hydrophilic cationic drug such as streptomycin. The biodegradable polymer may be chitosan. A pharmaceutical preparation containing the nanoparticles is administered to a patient orally and the nanoparticles release the drug in vivo. The drug can be complexed with a naturally occurring polymer, such as dextran sulfate. The drug, optionally complexed, is mixed with the biodegradable polymer followed by an inorganic polyanion to form the nanoparticle. In one example, the nanoparticles were about 560 nm in average size, had a zeta potential of about +54 mV and were used to treat tuberculosis in mice.

U.S. Pat. No. 7,550,441 to Farokhzad et al. describes a conjugate that includes a nucleic acid ligand bound to a controlled release polymer system contained within a pharmaceutical compound. Some examples of the polymer system are based on poly(lactic) acid (PLA) and have mean particle sizes ranging from 137 to 2805 nm. The ligands have an affinity for a target and are prepared through the Systemic Evolution of Ligands by Exponential Enrichment (SELEX) process.

US Patent Publication 2009/0312402 to Contag et al. describes nanoparticles with encapsulated nucleic acid. The polymer may be PLA, PLG or PLGA and PEG. The particles may have ligands or antibodies attached to them for targeting the nanoparticles to a site of interest. The nanoparticles may have a polymer coating to provide controlled release. The particles are in the size range of about 50 nm to about 500 nm, with most of them in the sub-200 nm range.

US Patent Publication 2011/0244048 to Amiji et al. describes a method of making a nanoparticle comprising combining an aqueous solution of a solubilized therapeutic agent with a water-soluble polymer comprising polyethylene glycol (PEG) and a fatty acid. These components self assemble into a nanoparticle. Various dextran based particles have means sizes ranging from 14 nm to 430 nm. The therapeutic agent may be doxorubicin.

U.S. Pat. No. 8,048,453 to Sung et al. describes nanoparticles of chitosan, poly-glutamic acid, and an active agent. The particles have a mean particle size between about 50 nm and 400 nm. The active agent may be insulin for the treatment of diabetes or an active for treating Alzheimer's disease. The nanoparticles may be freeze-dried and loaded into a capsule for oral administration.

INTRODUCTION TO THE INVENTION

The following introduction is intended to introduce the reader to the invention and the detailed description to follow and not to limit or define the claims.

This specification describes a nanoparticle based delivery device. The device may be used for the treatment of various indications or for other purposes. However, this specification will primarily describe the use of the device to deliver chemotherapeutic drugs, for example, for the treatment of cancer.

The delivery device described in this specification includes a nanoparticle that is made predominantly from a biopolymer, for example a starch comprising amylose, amylopectin or both. The biopolymer may have its crystal structure broken, for example by shear forces and intensive mixing in the presence of a hydroxilic solvent, or by other methods. After the crystal structures have been broken, a crosslinking agent is added to stabilize the resulting biopolymer nanoparticles. The resulting nanoparticles comprise, for example, crosslinked high molecular weight starch polymer that can be handled as dry agglomerated particles. The dry particles can be dispersed in an aqueous medium to produce a stable latex dispersion of crosslinked hydrogel nanoparticles.

The inventors believe that these crosslinked biopolymer nanoparticles have attributes that make them useful as a drug delivery device. In an aqueous medium, the crosslinked biopolymer nanoparticles form a stable dispersion of swollen crosslinked biopolymer hydro-colloid particles. The crosslinked biopolymer nanoparticles swell by taking water into the core of the particle. This mechanism may be used to load an active agent, into the core of the crosslinked biopolymer nanoparticles. Loading of the active agent into the core of the crosslinked biopolymer nanoparticles also allows unloading, or release, of the drug, for example at, near or within target cells. In one example, the active agent is a chemotherapy drug that is released at, near or within cancer cells. Optionally, the crosslinked biopolymer nanoparticles that are loaded with the drug can be administered as a liquid suspension or dried to produce a powder.

One useful attribute of the crosslinked biopolymer nanoparticles is that they can be broken down by chemical and enzymatic elements, but they may persist in the body long enough to provide a sustained release of the active agent. While native starch particles would typically survive for less than 30 minutes in the body, starch-based crosslinked biopolymer nanoparticles have a considerably longer half-life. In a related attribute, the nanoparticles may provide two mechanisms for releasing a loaded active agent. According to a first mechanism, the active agent is released from a generally intact crosslinked biopolymer nanoparticle. According to a second mechanism, the crosslinked biopolymer nanoparticle can degrade and release more of the drug. This second mechanism provides a sustained release of the drug, which is useful for active agents that require several hours or more of residence time for an optimal effect.

Another attribute of the crosslinked biopolymer nanoparticles is that the biopolymers are compatible with the body and ultimately can be reabsorbed. The biopolymers and their metabolites are nontoxic. In contrast, some synthetic polymers can cause side effects when used as a drug delivery device. For example, polyanhydride copolymers used for drug delivery have been associated with tissue inflammation and an enhanced rate of infections. These side effects may be due to the synthetic copolymers degrading via hydrolysis and yielding acidic functionalities. Starch, however, is ordinarily a food source and can be taken up by the body and degraded essentially without complications.

Another useful attribute of the crosslinked biopolymer nanoparticles is their size, and the narrow particle size distribution range within a given sample. In particular, the crosslinked biopolymer nanoparticles are predominantly in the range of 50-150 nm. Particles outside of this size range may be removed from the body through passive processes, such as through capillary wall passage, or more active processes, such as by the reticuloendothelial system (RES).

Yet another useful attribute of the nanoparticles is that the biopolymers may be functionalized. For example, amylose and amylopectin molecules may be oxidized and provided with carboxyl functionalities. In this example, the functionalized, crosslinked biopolymer nanoparticles have a more negative zeta potential which aids in the loading of some active agents. Optionally, the functionalizing reactions may allow attaching of targeting molecules, such as antibodies or ligands, to the crosslinked biopolymer nanoparticles. For example, the targeting molecule may be an aptamer that attaches, for example via a carbodiimide linkage, directly to the surface of a crosslinked biopolymer nanoparticle. The selection of specific aptamers, for example nucleotide or peptide aptamers, may direct, or facilitate, interactions between the crosslinked biopolymer nanoparticles and target cells. Other forms of functionalization may influence the release profile of the active agent.

The inventors have further observed that the degree of crosslinking of the starch nanoparticle influences the release profile of the active agent from a crosslinked biopolymer nanoparticles drug delivery system. In one example, a drug delivery system comprises biopolymer nanoparticles that are crosslinked. The crosslinked biopolymer nanoparticles may be functionalized to facilitate loading of an active agent and to attach a targeting molecule, such as an aptamer. The conjugated crosslinked biopolymer nanoparticles are loaded with an active agent. In this example, the size of the crosslinked starch nanoparticle may provide a longer systemic viability. The longer systemic viability may increase the likelihood of an interaction between the targeting molecule and a target cell. Upon a successful interaction, the drug delivery system may cross the phospholipid bilayer and enter the target cell, through receptor-mediated transport or otherwise. The degree of crosslinking of the biopolymer nanoparticles may provide a desired release profile of the loaded drug into the target cell. Optionally, the amount of attached targeting molecule may be varied to increase or decrease the rate of target cell uptake of the drug delivery system. Further optionally, the crosslinked biopolymer nanoparticle may be used without a targeting molecule.

The inventors have further observed that the amount of targeting molecule that is attached to the crosslinked biopolymer nanoparticle influences the uptake by the target cell.

The drug delivery system provides the ability to specifically tailor the targeting molecule to a specific target cell, for example a specific type of cancer cell. The rate of uptake of the drug delivery system can also be tailored based upon the amount of the targeting molecule that is attached. The drug delivery system provides the ability to tailor the active agent that is delivered directly into the target cell, for example an anti-cancer, chemotherapy drug. The drug delivery system further provides the ability to tailor the release profile of a tailored drug to optimize the effect of the active agent, for example, by varying the degree of crosslinking to prolong or shorten the release profile.

An example drug delivery device may have: 1) a nanoparticle comprising crosslinked biocompatible or resorbable polymers, the polymers modified after the particle was formed by chemical or enzymatic modification, 2) an encapsulated therapeutically active agent within the colloidal hydrogel, and, optionally, 3) an aptamer attached to the crosslinked polymers. The nanoparticles may be colloidal hydrogel starch particles.

A medicament described in this specification comprises a plurality of crosslinked nanoparticles, the nanoparticles are made up mostly of high molecular weight starch with an active agent conjugated to at least some of the nanoparticles. Optionally, the nanoparticles may include a targeting molecule. The medicament may be useful in the treatment of cancer. A method of making a medicament comprises the steps of forming a plurality of high molecular weight, starch-based nanoparticles, wherein the nanoparticles having a size predominantly in the range of 50 to 150 nm and are crosslinked to a degree selected to provide a desired active agent release profile and loading an active agent within the nanoparticles. Optionally, the nanoparticles can be functionalized to increase loading of the active agent or attach a targeting molecule or both.

A compound described in this specification comprises a high molecular weight starch based nanoparticle core having a size in the range of 50 to 150 nm, a drug and, optionally, an aptamer targeting molecule. The compound may be used for the treatment of cancer.

BRIEF DESCRIPTION OF THE DRAWINGS

FIG. 6 is a schematic representation of minor swelling in an SB latex particle and significant swelling of the crosslinked biopolymer nanoparticles of FIG. 2 in an aqueous dispersion, illustrating the hydrocolloid structure of the starch based nanoparticles.

DETAILED DESCRIPTION

Target Particle Size

Figure 1:
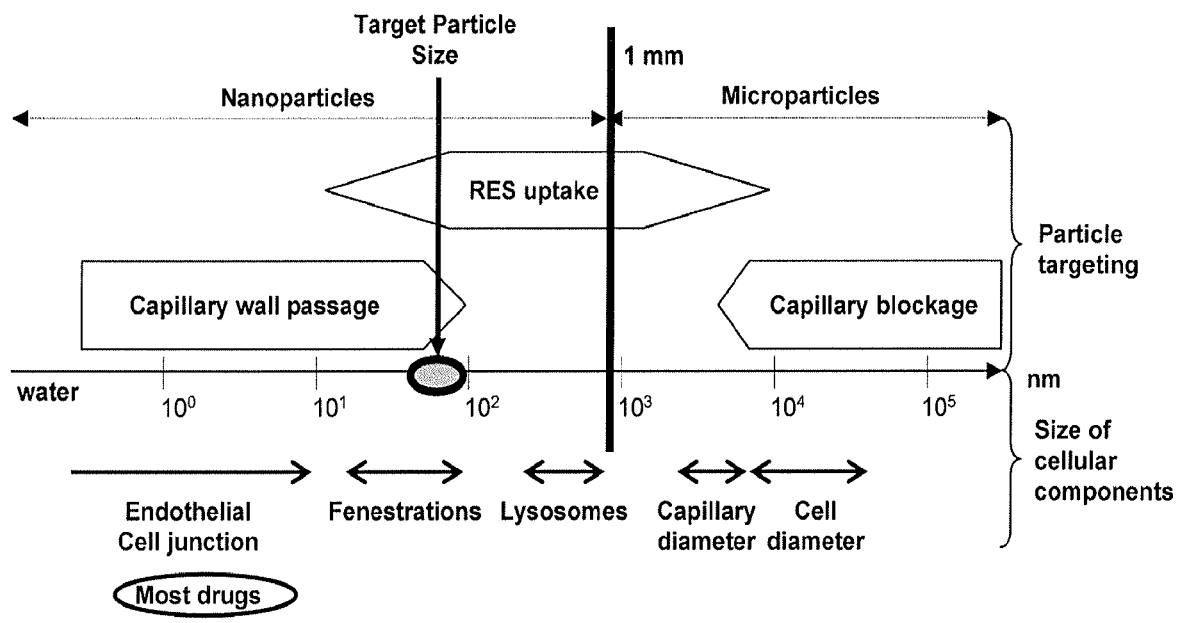
FIG. 1 is a chart showing a target particle size relative to particle removal mechanisms.

Referring to FIG. 1, particle size plays a role in determining the fate of a drug or a drug delivery mechanism after administration. Without intending to be bound by any particular theory of operation, particles having a size in the range of about 50 to 150 nm may enjoy longer systemic circulation as a result of being within this size range, independent of other properties of the particle such as surface density or hydrophilicity which may also affect uptake by the reticuloendothelial system (RES).

The term biopolymer nanoparticle will be used in this specification to refer to a form of a biopolymer in which the native structure of the biopolymer source material has been substantially removed but multiple molecules of the biopolymer are complexed to form discrete particles, for example by way of cross-links between molecules within the particles. Crosslinked biopolymer nanoparticles 10 can be made by various processes.

The presence of biopolymer nanoparticles can be determined by observation under a scanning electron microscope (SEM); detecting particle sizes larger than individual molecules by DLS or NTA measurements; or, observing a maximum swelling value (alternatively called a volume factor or swell ratio) in a very dilute dispersion of the biopolymer nanoparticles that is less than the swell ratio of the native or dissolved form of the biopolymer. Regarding the last technique, the swell ratio of native starch granules is about 32 and the swell ratio of cooked (dissolved) starch is about 44. In comparison, the swell ratio of starch nanoparticles may be between about 2 and 20 with lower swell ratios corresponding to more tightly cross-linked particles. A method of determining swell ratio is described in the examples section herein and in International Application No. PCT/CA2012/050375 which is incorporated herein by this reference to it. Biopolymer nanoparticles useful as a drug delivery device may have a swell ration between about 2 and 20, between about 6 and 18 or between about 6 and 16.

Waxy corn starch is a preferred bio-based material due to its resistance to retrograding after it has been processed relative to other starches. Waxy corn starch also produces nanoparticles with less cross-linker or without added cross-linker.

In one example, the biopolymer nanoparticles 10 are made according to a process described in U.S. Pat. No. 6,677,386 (which corresponds to International Publication WO 00/69916), which is incorporated herein by reference. In this example process, a biopolymer feed stock, such as starch comprising amylose or amylopectin or both, is combined with a plasticizer. This combination is mixed under high shear forces, preferably in a twin screw fully intermeshing co-rotating extruder, to plasticize the biopolymer and create a thermoplastic melt phase in which the crystalline structure of the biopolymer is removed. A crosslinking agent is then added, while mixing continues, to form the crosslinked biopolymer nanoparticles 10. The crosslinked biopolymer nanoparticles 10 exit the extruder as a strand of extrudate, which is ground to a fine dry powder. The crosslinked biopolymer nanoparticles 10 are present in the powder in an agglomerated form, and can be dispersed in an aqueous medium. One example of crosslinked biopolymer nanoparticles 10 made by this process is the commercially available EcoSphere® 2202 from EcoSynthetix Inc. of Burlington, Ontario, Canada.

The biopolymer feed stock may be starch or other polysaccharides such as cellulose and gums, as well as proteins (e.g. gelatin, whey protein). The biopolymers may also be previously modified, e.g. with cationic groups, carboxymethyl groups, by acylation, phosphorylation, hydroxyalkylation, oxidation and the like. Starch and mixtures of at least 50% starch with other polymers are preferred. The starch, whether used alone or in a mixture, is preferably a high molecular weight starch, for example a molecular weight of at least 10,000, and not dextran or dextrin. For example, the starch can contain amylose, amylopectin, or both. Waxy starches, such as waxy cornstarch, are particularly preferred.

The following paragraphs are repeated or summarized from U.S. Pat. No. 6,677,386 to further describe a process of making the nanoparticles.

The biopolymer preferably has a dry substance content of at least 50% by weight at the time when processing starts. Processing is preferably done at a temperature of at least 40 degrees C., but below the degradation temperature of the polymer, for example 200 degrees C. The shear can be affected by applying at least 100 J of specific mechanical energy (SME) per g of biopolymer. Depending on the processing apparatus used the minimum energy may be higher; also when non-pregelatinised material is used, the minimum SME may be higher, e.g. at least 250 J/g, especially at least 500 J/g.

The plasticiser may water or a polyol (ethyleneglycol, propyleneglycol, polyglycols, glycerol, sugar alcohols, urea, citric acid esters, etc.). The total amount of plasticisers (i.e. water and others such as glycerol) is preferably between 15 and 50%. A lubricant, such as lecithin, other phospholipids or monoglycerides, may also be present, e.g. at a level of 0.5-2.5% by weight. An acid, preferably a solid or semi-solid organic acid, such as maleic acid, citric acid, oxalic, lactic, gluconic acid, or a carbohydrate-degrading enzyme, such as amylase, may be present at a level of 0.01-5% by weight of biopolymer. The acid or enzyme assists in slight depolymerisation, which is assumed to be advantageous in the process of producing nanoparticles.

The crosslinking is preferably at least in part reversible, i.e. the crosslinks are partly or wholly cleaved during the mechanical treatment step. Examples of reversible cross-linkers are a) dialdehydes and polyaldehydes, which form more stable full acetals and reversibly form hemiacetals, and b) anhydrides and mixed anhydrides, which form ester linkages (e.g. succinic and acetic anhydride) and the like. Suitable dialdehydes and polyaldehydes are glutaraldehyde, glyoxal, periodate-oxidised carbohydrates, and the like.

Such crosslinkers may be used alone or as a mixture of reversible crosslinkers, or as a mixture of reversible and non-reversible crosslinkers. Thus, conventional crosslinkers such as epichlorohydrin and other epoxides, triphosphates, divinyl sulphone, can be used as non-reversible crosslinkers for polysaccharide biopolymers, while dialdehydes, thiol reagents and the like may be used for proteinaceous biopolymers. The crosslinking reaction may be acid- or base-catalyzed. The level of crosslinking agent can conveniently be between 0.1 and 10 weight % with respect to the biopolymer. The crosslinking agent may be present at the start of the mechanical treatment, but in case of a non-pre-gelatinised biopolymer such as a starch with native starch granules, it is preferred that the crosslinking agent is added later on, i.e. during the mechanical treatment.

The mechanically treated, crosslinked biopolymer is then formed into a latex by dispersion in a suitable medium, usually water and/or another hydroxylic solvent such as an alcohol), to a concentration of between 4 and 50 weight % especially between 10 and 40 wt. %. Prior to the dispersion a cryogenic grinding step may be performed, but stirring with mild heating may work equally well. This treatment results in a gel which either spontaneously or after induction by water adsorption, is broken into a latex. This viscosity behavior can be utilised for applications of the particles, such as improved mixing, etc. If desired, the dispersed biopolymer may be further crosslinked, using the same or other crosslinking agents as describe above. The extrudate is characterised by swelling in an aqueous solvent, e.g. water or a mixture of at least 50% water with a water-miscible solvent such as an alcohol, and by exhibiting a viscosity drop afterwards to produce a dispersion of nanoparticles.

International Patent Application Publication No. WO 2008/022127 A2 and its equivalent US Patent Application Publication Number 2011/0042841 A1 describe a process for producing biopolymer nanoparticles in large quantities. US Patent Application Publication Number 2010/0143738 A1 describes a process for producing biopolymer nanoparticles conjugative with additives during the extrusion process. US Patent Application Publication Numbers 2010/0143738 A1 describes a process for producing biopolymer nanoparticles conjugated with additives during the extrusion process. These publications are incorporated herein by reference.

The production of biopolymer nanoparticles similarly formed by reactive extrusion and comprising starch essentially without crystalline structures is described in *Starch nanoparticle formation via reactive extrusion and related mechanism study*, Delong Song et al., Carbohydrate Polymers 85 (2011) 208-214. The contents of this publication are incorporated herein by reference. This publication is incorporated herein by reference. Using various materials and reaction conditions, dispersions having particles with number average particle sizes up to about 2000 nm were produced. Various other methods of making biopolymer nanoparticles are also summarized in this paper.

Another method reported to produce biopolymer nanoparticles by reactive extrusion process from waxy corn starch is described in International Publication Number WO 2011/071742 A2, Process for Preparing Stable Starch Dispersions, by Welsch et al., published on Jun. 16, 2011. This publication is incorporated herein by reference. This process comprises introducing a feed starch and an hydroxylc liquid to an extruder. Shear forces are applied in the extruder to the starch and the liquid in the substantial absence of a crosslinker under conditions sufficient to prepare a stable dispersion of starch particles in the hydroxylic liquid.

Another method reported to produce biopolymer nanoparticles is described in International Publication Number WO 2011/155979 A2, Process for Preparing Stable Dispersions of Starch Particles, by Welsch et al., published on Dec. 15, 2011. The contents of this publication are incorporated herein by reference. In this process, a feed starch and an aqueous liquid are introduced into a rotor stator mixer. The feed starch and aqueous liquid are maintained in the rotor stator mixer at a temperature ranging from a gelation temperature to less than a solubilization temperature. The feed starch is sheared into starch particles with the rotor stator mixer to form the dispersion of starch particles in the aqueous liquid.

Another method of producing a starch nanoparticle is described in U.S. Pat. No. 6,755,915 to Van Soest et al. (Jun. 29, 2004) which teaches a method of preparing starch particles with a size range of 50 nanometers to 100 microns. The disclosure of this patent document is incorporated herein by reference. The method includes the steps of: dispersing starch in a first water phase; dispersing a second hydrophobic phase in the first phase to form an oil-in-water emulsion; inverting the oil-in-water emulsion to a water-in-oil emulsion; crosslinking the starch in the first phase; and separating the formed starch particles. The phase inversion can occur by including a surfactant that stabilizes a water-in-oil emulsion or the surfactant can be temperature sensitive and increasing the reaction temperature. The inversion can also occur by the addition of further hydrophobic liquids or various suitable salts. In this process the starch molecules can remain partially granular during both the crosslinking reaction and complete gelatinisation of the granular starch can be effected before, during or after the phase inversion. Gelatinization occurs by increased temperature, salts or combinations thereof.

Another method reported to produce biopolymer nanoparticles is described in WO 2010/084088 to Santander Ortegea et al. (international publication Jul. 29, 2010). The contents of this publication are incorporated herein by reference. The method includes the steps of preparing starch derivatives by a first disintegration step, with solvent and increased temperatures, followed by common substitution methods, such as esterification, etherification. The starch derivatives are added to an organic solvent and an oil/water emulsion is prepared with a high shear mixer. Sonication may be used to improve the oil droplet distribution. The organic phase is then removed through a membrane, which results in an aqueous dispersion of starch-based nanoparticles.

Another method of making biopolymer nanoparticles is described in WO 2010/065750 to Bloembergen et al. which teaches that Brabender static high shear mixers and Sigma Blade mixers may be used in place of an extruder to produce nanoparticles by way of shearing starch granules in the presence of a crosslinker. The contents of this publication are incorporated herein by reference.

Alternatively, fragmented particles may be used. British patent GB 1420392, for example, describes a method of producing fragmented starch particles that are partially cross-linked and partially crystalline or soluble that may be used as an alternative to nanoparticles. Nanoparticles are preferred, however, since they are likely to be less prone to retrogradation.

The process can be operated to produce particles that have a number average particle size in the range of 50 to 150 nm and which, considering a distribution of their particle sizes, are also predominantly in the range of 50 to 150 nm in size. Such particles include, for example, EcoSphere® 2202 particles commercially available from Ecosynthetix Inc. of Burlington, Ontario, Canada and EcoSynthetix Ltd. of Lansing, Mich., USA. These products are made primarily from starch including amylose and amylopectin. The product is normally sold to replace petroleum based latex binders in industrial applications, such as coated paper and paperboard. The product is provided in the form of a dry powder of agglomerated nanoparticles with a volume mean diameter of about 300 microns. When mixed in water and stirred, the agglomerates break apart and form a stable dispersion of the nanoparticles.

Figure 2A:
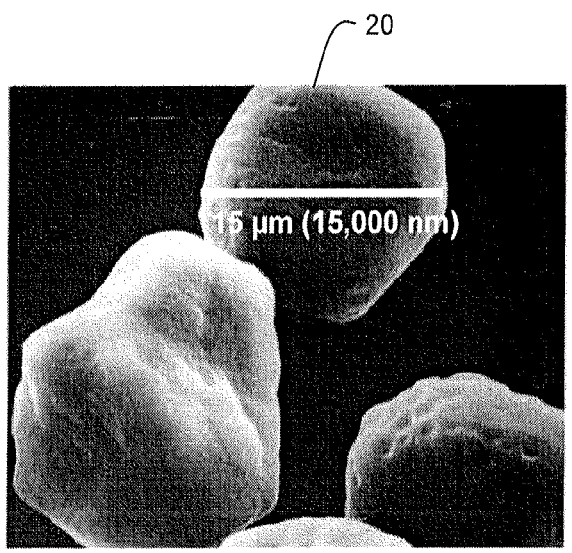
FIG. 2A shows an electron microscopy image of native corn starch granules.
Figure 2B:
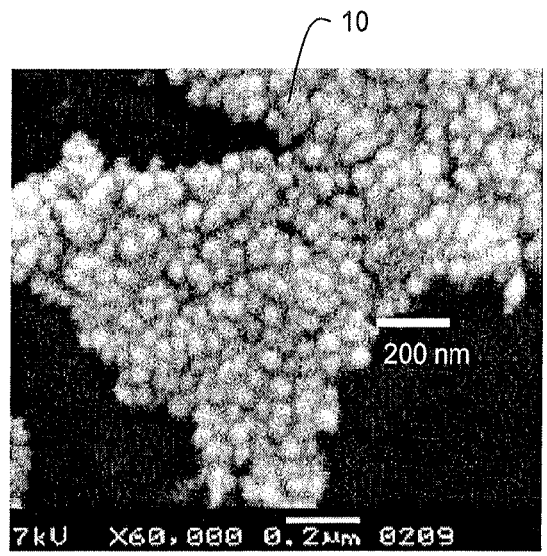
FIG. 2B shows an electron microscopy image of example crosslinked biopolymer nanoparticles, referred to as EcoSphere® 2202.

Comparing FIG. 2A to FIG. 2B, the EcoSphere® 2202, as an example of crosslinked biopolymer nanoparticles 10, are about 100 to 300 times smaller than native starch granules 20. Whereas a starch granule 20 may be 15 microns in size, the nanoparticles 10 are clearly well under 200 nm in size. Accordingly, the effective surface area of the nanoparticles 10 is much greater, for example 200 $m^2/g$ or more.

Figure 3:
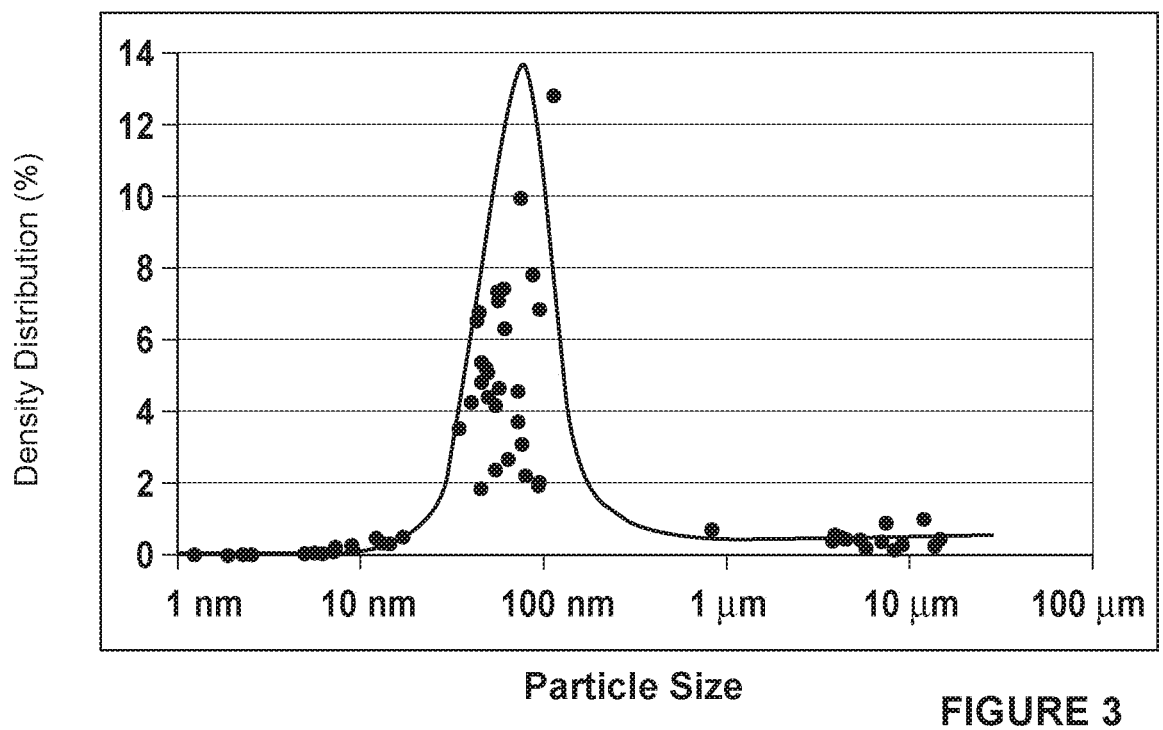
FIG. 3 shows an analysis of particle size for an aqueous dispersion of the crosslinked biopolymer nanoparticles of FIG. 2 by Dynamic Laser Light Scattering (DLS).
Figure 4:
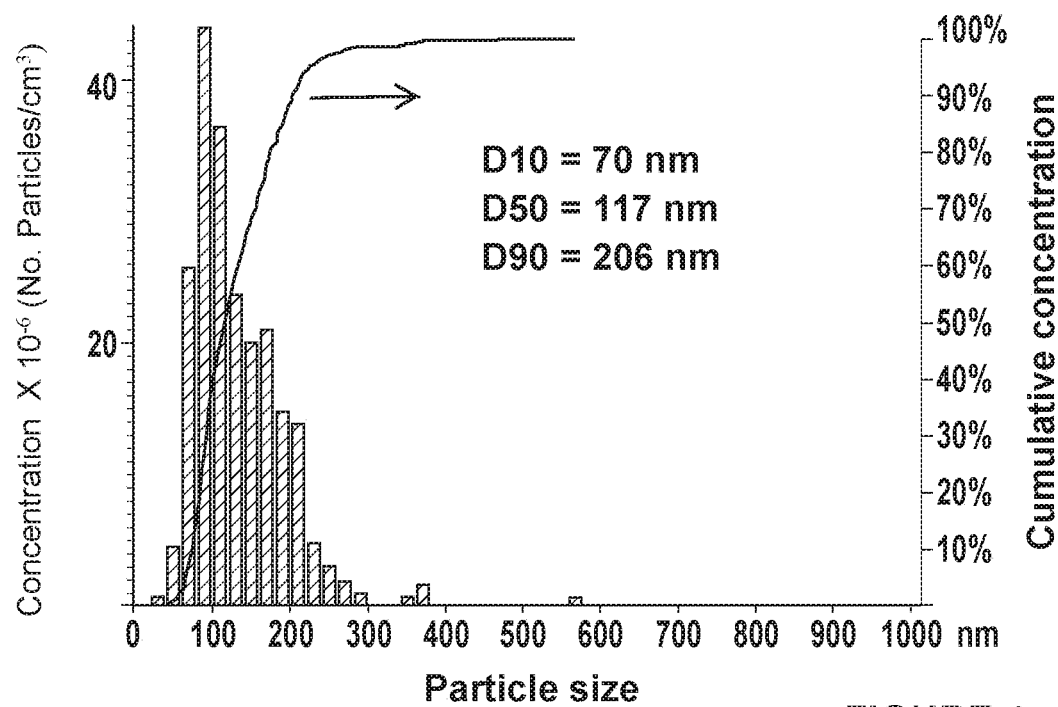
FIG. 4 shows an analysis of particle size for an aqueous dispersion of the crosslinked starch nanoparticles of FIG. 2 by Nanoparticle Tracking Analysis (NTA).

FIGS. 3 and 4 illustrate particle size measurements of an aqueous dispersion of the EcoSphere® 2202, as an example of crosslinked biopolymer nanoparticles 10, by Dynamic Laser Light Scattering (DLS) and by Nanoparticle Tracking Analysis (NTA), respectively. These two techniques are complementary, given that the NTA technique is a direct measurement of the diffusion coefficient for individual particles tracked via video tracking software (and relates that to particle diameter via the Stokes-Einstein equation), and can measure particles in the range of 50-1000 nm, while DLS can measure to smaller particle sizes below 50 nm. Other techniques, including oscillating probe Atomic Force Microscopy (AFM), Scanning Electron Microscopy (SEM), Environmental SEM (ESEM), Transmission Electron Microscopy (TEM) and Scanning/Transmission Electron Microscopy (STEM), all provided similar particle size images consistent with the data in FIGS. 3 and 4.

Referring to FIG. 3, most of the EcoSphere® 2202 particles have a size in the range of about 50 to 100 nm. As indicated in the NTA measurements, most of the particles (D50) are under 120 nm in size and there are virtually no particles larger than 400 nm. Any particles larger than 1000 nm would be removed quickly from the body causing no harm but wasting some of an intended dosage of the drug. Accordingly, if a sample includes material amounts of particles over 1000 nm in size, these may be removed by filtration, or otherwise, before an active agent 22 is loaded into the nanoparticles.

Figure 5:
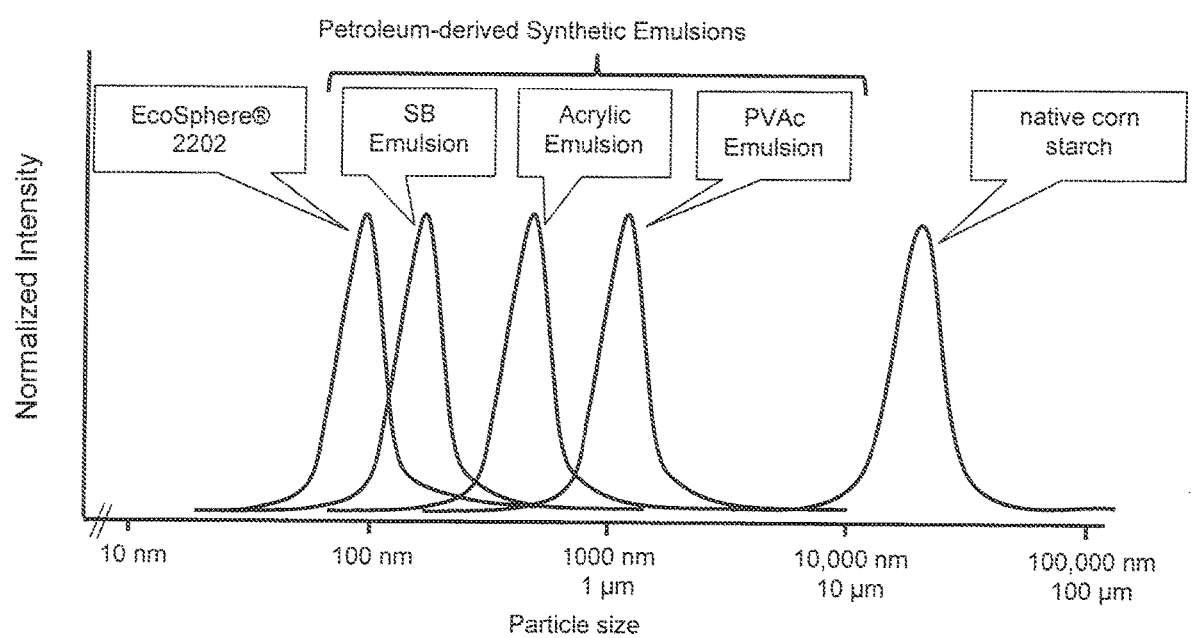
FIG. 5 is a schematic graph comparing particle sizes for the crosslinked biopolymer nanoparticles of FIG. 2, synthetic polymer colloids and native corn starch.

Referring to FIG. 5, the crosslinked biopolymer nanoparticles 10 are generally smaller than particles found in synthetic latex emulsions such as styrene-butadiene (SB) emulsions, acrylic emulsions and polyvinyl acetate (PVAc) emulsions. The crosslinked biopolymer nanoparticles 10 have a narrow size-distribution, with a polydispersity index of about 30%, and properties characteristic of polymer colloids. Since the crosslinked biopolymer nanoparticles 10 are predominantly in the size range of about 50 to 150 nm (for example 50% or more of the nanoparticles by number or mass may be in this range) the crosslinked biopolymer nanoparticles 10 may be cleared more slowly from the systemic circulation (liver, spleen) than is the case of larger particles. The crosslinked biopolymer nanoparticles 10 may have hydrophilic properties, which may further inhibit removal by the RES. The degradation products of the starch nanoparticles (D-glucose and maltodextrans) are non-toxic. The additional natural materials and chemicals that are used to make the starch crosslinked biopolymer nanoparticles are also relatively non-toxic.

The crosslinked biopolymer nanoparticles 10 are not water soluble, but instead form a stable latex dispersion of swollen hydrogel colloidal crosslinked particles in water.

FIGS. 6A and 6B depict the latex dispersion consisting of water-swollen crosslinked biopolymer nanoparticles 10, which can de-swell with increasing solids. This permits dispersions that can be made at higher solids. In contrast, the particles in synthetic latex emulsions do not swell nor contain a substantial portion of water inside the colloid particles. The swelling characteristics of typical SB latex and colloids of biopolymer nanoparticles have been compared and reported in a number of articles (see Do lk Lee, Steven Bloembergen, and John van Leeuwen, "Development of New Biobased Emulsion Binders", PaperCon2010, "Talent, Technology and Transformation", Atlanta, Ga., May 2-5, 2010; and, Steven Bloembergen, Edward VanEgdom, Robert Wildi, Ian. J. McLennan, Do lk Lee, Charles P. Klass, and John van Leeuwen, "Biolatex Binders for Paper and Paperboard Applications", Journal of Pulp and Paper Science, 36, No 3-4, p. 151-161, 2011; J. Y. Shin, N. Jones, D. I. Lee, P. D. Fleming, M. K. Joyce, R. DeJong, and S. Bloembergen, "Rheological Properties of Starch Latex Dispersions and Starch Latex-Containing Coating Colors", TAPPI, PaperCon 2012, "Growing the Future", New Orleans, La., Apr. 21-25, 2012). The contents of these publications are incorporated herein by reference.

Figure 7:
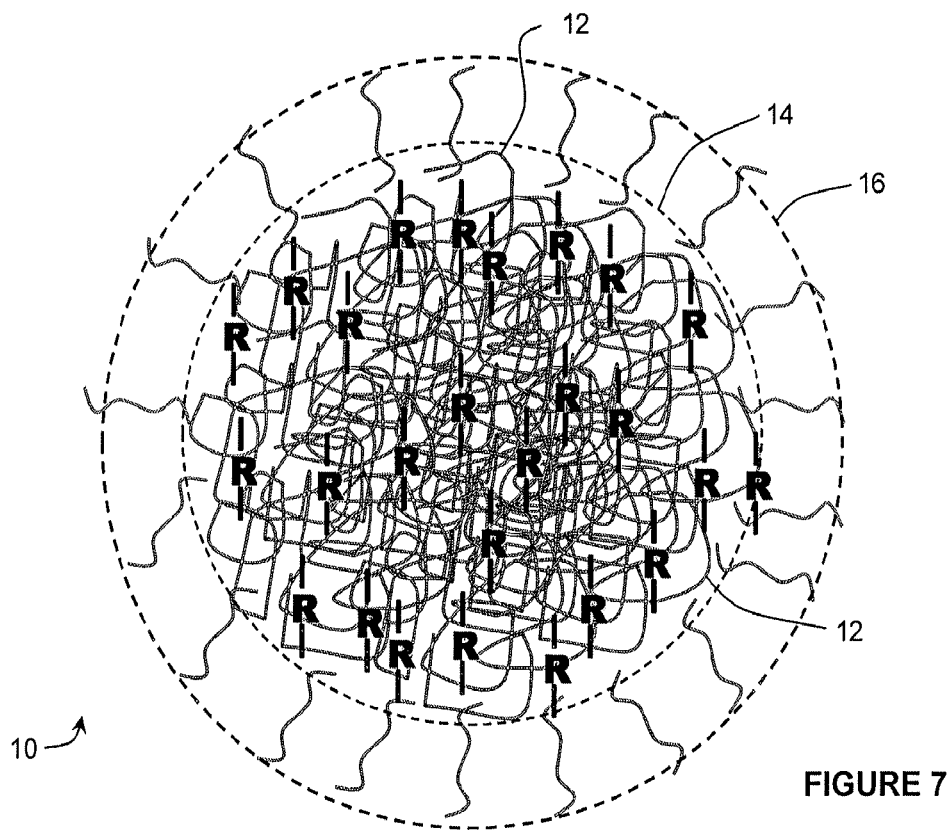
FIG. 7 is a schematic model of an example crosslinked biopolymer nanoparticle.

FIG. 7 illustrates a schematic model for the crosslinked biopolymer nanoparticles 10. The crosslinked biopolymer nanoparticles 10 can be thought of as one crosslinked macromolecular unit, with —R— representing an intermolecular crosslink between individual biopolymers 12. Other types of crosslinked structures may exist, such as intramolecular crosslinks.

The crosslinked biopolymer nanoparticles 10 comprise a core 14 and a shell 16. The core 14 receives and releases water as it swells and de-swells and the shell 16 provides a steric stabilization mechanism for the dispersed colloid particles. Water is released, bound and adsorbed from the core 14 through the shell 16. The structure of the crosslinked biopolymer nanoparticles 10 is further described in Steven Bloembergen, Ian. J. McLennan, John van Leeuwen and Do lk Lee, "Specialty Biobased Monomers and Emulsion Polymers Derived from Starch", 2010 PTS Advanced Coating Fundamentals Symposium, Munich, Germany, Oct. 11-13, 2010.

Aqueous dispersions of the crosslinked biopolymer nanoparticles 10 are stable for up to 12 months or longer. Because typical native starches contain very high molecular weight amylopectin polymer (millions of daltons) and high molecular weight amylose polymer (hundreds of thousands of daltons), solutions up to 5 or 10% solids can have very high gel-like viscosities. Commercial dispersions of corn starch granules typically reach up to about 30% solids or higher, because these products have been chemically, thermally or enzymatically treated to reduce their molecular weight in order to attain higher solids contents. This is the typical molecular weight/solids trade off that one faces to maintain a reasonably low viscosity for polymer solutions. Purer dispersions with higher solids content (up to about 40% solids), and ultra-high solids formulations (up to 72% solids) have been developed using the crosslinked biopolymer nanoparticles 10. This may be beneficial for drug delivery applications, where a high solids concentration facilitates loading of greater amounts of the active agent 22 into the crosslinked biopolymer nanoparticles 10.

The crosslinked biopolymer nanoparticles 10 may be loaded with an active agent 22, for example a drug, or other agent, and used as a delivery device. Loading of the active agent 22 may also be referred to as conjugating or encapsulating.

As discussed above, the core 14 of the nanoparticles takes in water as it swells. Similarly, small molecules, such as some drugs, or other agents can be taken up, adsorbed, or otherwise loaded into the core of the nanoparticles. An example presented further below will describe loading of the drug doxorubicin in the crosslinked biopolymer nanoparticles 10 by a phase separation method (Example 1) and by ethanol precipitation (Example 4). By itself, doxorubicin has been linked to acute cardiotoxicity which limits its use. In other experiments, Carmustine and BCNU (bis(chloroethylnitrosourea)) have been also been loaded into the crosslinked biopolymer nanoparticles 10.

It can be expected that other methods of loading the drug may also be used, and that other drugs and agents can similarly be loaded. For example, other active agents 22 may include cyclophosphoramide and camptothecins that may be loaded into the crosslinked biopolymer nanoparticle 10 and, like doxorubicin, make the crosslinked biopolymer nanoparticles 10 useful in the treatment of cancer. The crosslinked biopolymer nanoparticles 10 may also encapsulate non-chemoactive agents, such as antisense oligonucleotides, peptides, and cytokines for other therapeutic applications.

After the active agent 22 is loaded, the crosslinked biopolymer nanoparticles 10 can be recovered by lyophilization, which results in a powder of the nanoparticles loaded with the encapsulated active agent 22. The powder can be mixed with water, or another hydroxylic solution, to disperse the crosslinked biopolymer nanoparticles 10 into a stable colloidal dispersion. The dispersion can be administered to treat a patient in the liquid form, for example orally, by intra-venous infusion or injection. The powder can be mixed with a pharmaceutical carrier and made into a solid or gelled drug product, such as a tablet or capsule. The drug product may be administered in any known manner used for pharmaceutical products, such as orally, rectally, transdermally and the like.

The biopolymers 12 may be modified, also referred to as functionalized, through chemical or enzymatic modifications before, during or after forming the crosslinked biopolymer nanoparticle 10. In principle, any chemical or enzymatic modification known for polysaccharides can be employed. For example, a summary of various chemical and enzymatic oxidation processes is provided in column 1, line 66 to column 3, line 50 in R. A. Jewel et al., U.S. Pat. No. 6,379,494, "Method of Making Carboxylated Cellulose Fibers and Products of The Method", Apr. 30, 2002, the disclosure of which is incorporated herein by reference. Although these methods are discussed in relation to cellulose, many if not all are adaptable to starch polymers.

In Example 4, a biopolymer 12 of starch is functionalized after the crosslinked biopolymer nanoparticles 10 are formed. In particular, the biopolymers 12 were oxidized to add carboxyl functional groups. While this is described in Example 4 as relating primarily to the attachment of a targeting molecule 18, to be discussed further below, functionalizing the crosslinked biopolymer nanoparticle 10 may also facilitate loading of the active agent 22.

Functionalizing the crosslinked biopolymer nanoparticle 10 by chemical or enzymatic methods may also attach other types of functional groups to the biopolymers to provide binding sites for the targeting molecule 18, the active agent 22 or both. The surface of the crosslinked biopolymer nanoparticles 10 may also be modified, chemically or otherwise to alter systemic clearance rates to provide a better control of the delivered active agent 22 and a targeted delivery, if any.

For example, the oxidation resulted in a change in the zeta potential of the crosslinked biopolymer nanoparticle 10. The zeta potential of a non-functionalized crosslinked biopolymer nanoparticle 10 is in the range of 0 to negative 6 mV. An oxidized crosslinked biopolymer nanoparticle 10 demonstrates a zeta potential of about negative 25 mV. The oxidation reaction may also be controlled to provide functionalized crosslinked biopolymer nanoparticles 10 that have an intermediate zeta potential value, for example between about negative 6 to about negative 25 mV. Tuning the zeta potential of the crosslinked biopolymer nanoparticles 10 may allow selective loading of the active agent 22 and, additionally, this tuning may provide control of the release profile of the active agent 22. Many small molecules being developed for cancer treatment are hydrophobic and lipophilic and, hence, they are difficult to dissolve. Functionalizing, for example by oxidative modification, or otherwise, of the crosslinked biopolymer nanoparticle 10 may enhance the ability of the small molecule, hydrophobic/lipophilic drugs to be loaded onto the crosslinked biopolymer nanoparticle 10.

While the water soluble TEMPO catalyst (2,2,6,6-tetramethylpiperidine-1-oxyl radical) used in Example 4 provided starch functionalities throughout the crosslinked biopolymer nanoparticle 10, an immobilized TEMPO catalyst causes only biopolymers 12, or portions of biopolymers 12, located at or near the shell 16 to be functionalized. This approach could be used, for example, to attach the targeting molecule 18 to the surface of the crosslinked biopolymer nanoparticle 10 with less modification of the zeta potential of the core 14. Optionally, a soluble catalyst can be used if a greater change in zeta potential is desired.

While any form of oxidation may be used, the TEMPO oxidation is preferred. The TEMPO catalyst is used to specifically modify the C6 hydroxyl of the glucopyranoside position to a carboxyl functionality. This process prevents the molecular weight reduction of the polysaccharide polymer that is common with many other oxidative processes.

Many functionalizing techniques are known to add aldehyde groups to polysaccharide polymers. Without intending to exclude the possibility that one of these functionalization techniques might be useful, they are not currently preferred. The aldehyde groups are reactive and tend to cause the crosslinked biopolymer nanoparticles 10 to agglomerate and stick together. This interferes with creating a colloidal dispersion, and so may also interfere with distribution of the crosslinked biopolymer nanoparticles 10 in the body.

As described above, the zeta potential of unmodified crosslinked biopolymer nanoparticles 10 is low, hence the observed colloidal stability is attributed mainly to steric stabilization. Without being bound by theory, the shell 16 contains short polysaccharide chains which project into the aqueous environment. These chains may function as a colloidal stabilizer for the crosslinked biopolymer nanoparticle 10 in water and as a partial hydrophilic shell for bound water. This in turn may prevent or slow the release, efflux or diffusion of hydrophobic active agents 22 from the crosslinked biopolymer nanoparticle 10.

In some of the examples provided below, doxorubicin was used as the active agent 22. The doxorubicin was loaded into the crosslinked biopolymer nanoparticles 10 so that the release profile could be followed using a fluorescence technique. This work has demonstrated a biphasic release profile with suitable release kinetics spanning multiple hours of sustained release of the doxorubicin. The fluorescence of the doxorubicin-loaded crosslinked biopolymer nanoparticles 10 declines over time but some fluorescence remains even after 12 hours. This indicates that not all of the doxorubicin is released from an intact particle. The remainder of the loaded doxorubicin, however, will be released in the body as the crosslinked biopolymer nanoparticle 10 degrades, for example due to alpha-amylase enzymes. The complete release time may be 24, 48, 72 hours or more. Other drugs or compounds that are used as the active agent 22 may demonstrate a similar sustained and biphasic release profile.

Figure 12:
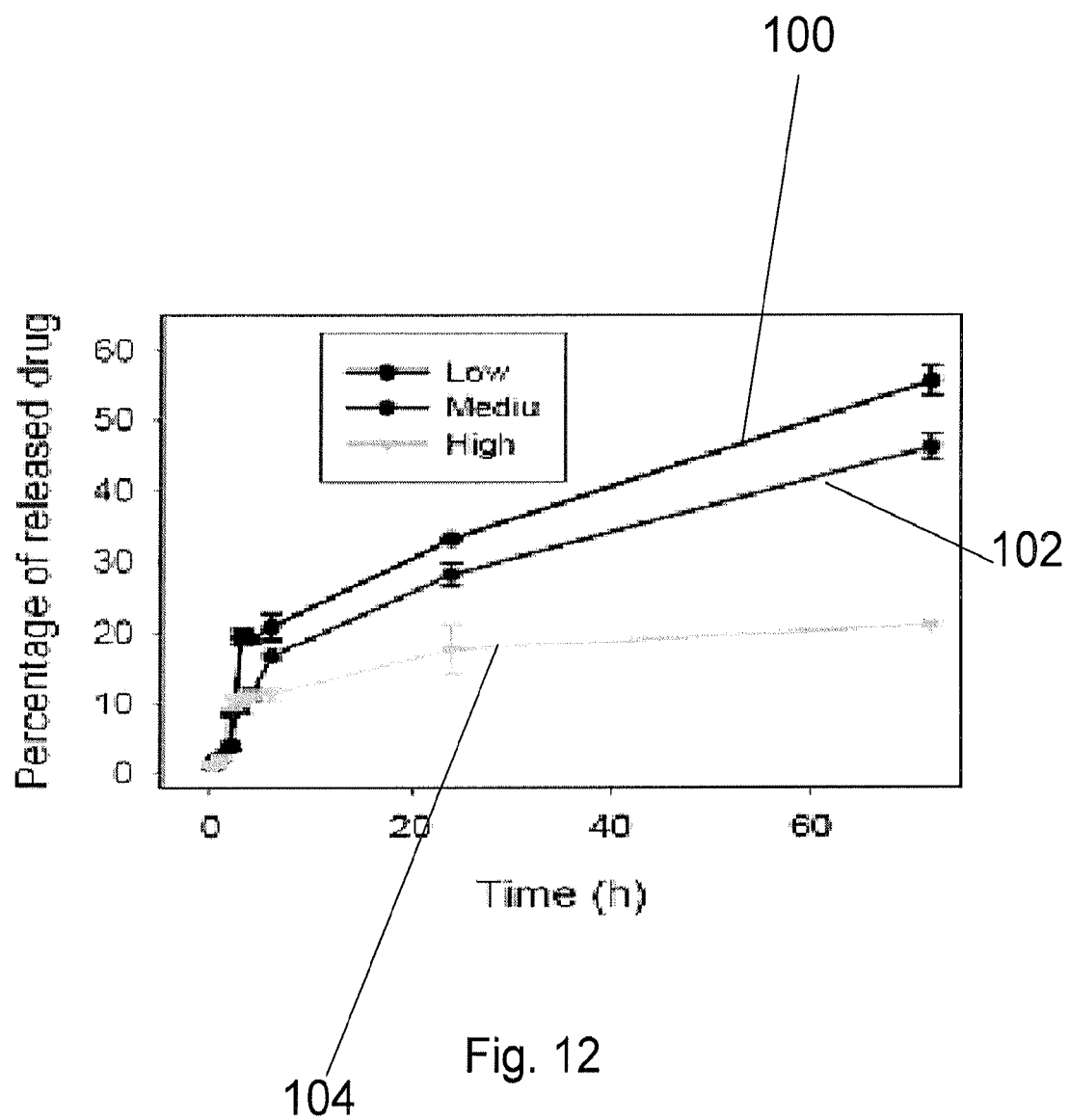
FIG. 12 is a chart showing the release profile of doxorubicin from biopolymer nanoparticles with different degrees of crosslinking.

Referring to FIG. 12, the inventors have observed a relationship between the degree of crosslinking of the biopolymer 12 and the release profile of the active agent 22. As described in Example 5, three different batches of crosslinked biopolymer nanoparticles 10 were produced, with relatively low, medium and high degrees of crosslinking. The greater the degree of crosslinking of the crosslinked biopolymer nanoparticle 10 the slower the rate of release of the active agent 22. In contrast, the batch of crosslinked biopolymer nanoparticles 10 that had a relatively lower degree of crosslinking demonstrated a faster rate of active agent 22 release.

In animal studies described in Example 3, doxorubicin loaded crosslinked biopolymer nanoparticles were used to treat glioblastoma multiforme, a primary brain tumor in athymic mice. These studies demonstrated a 30% increase in survival for the mice treated with doxorubicin-loaded crosslinked biopolymer nanoparticles 10 relative to the appropriate controls. Without intending to limit the invention to any particular theory, this success is attributed to one or more of several factors including the size, the surface properties, and the sustained release kinetics of the crosslinked biopolymer nanoparticles 10. The encapsulated doxorubicin is believed to enter the cell via endocytosis due to the relatively small size of the nanoparticle, while the free drug is metabolized and excreted.

Figure 11:
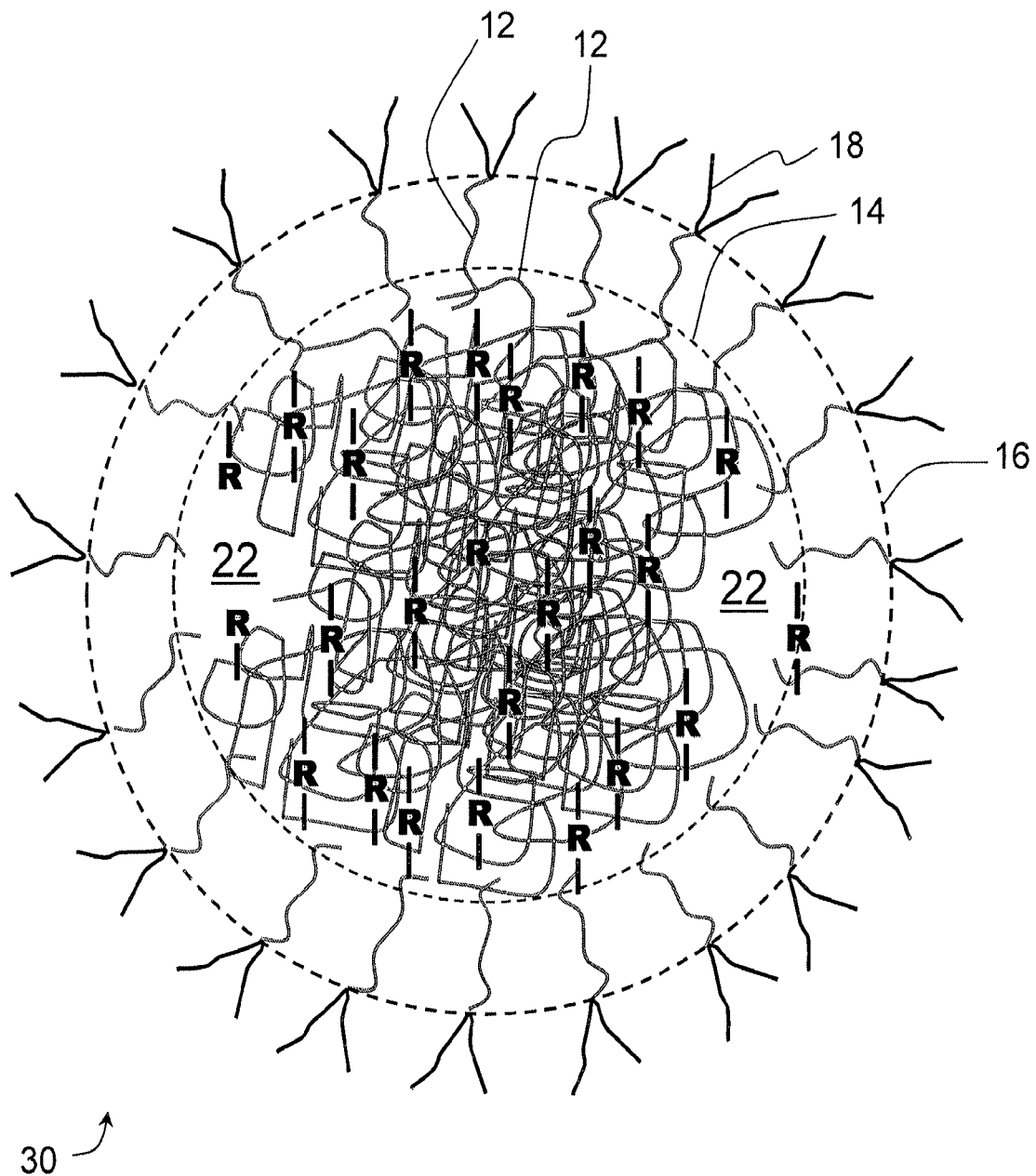
FIG. 11 is a schematic model of a crosslinked biopolymer nanoparticle of FIG. 2 conjugated with a drug and an aptamer.

FIG. 11 is a schematic of an example bioconjugate device 30 comprising a crosslinked biopolymer nanoparticle 10, a functionalized biopolymer 12, an optional targeting molecule 18 and a loaded active agent 22, that is shown within the core 14. FIG. 11 is merely a schematic and is not a representation or limitation of how the active agent 22 may be loaded in the bioconjugate device 30.

The bioconjugate device 30 may be used for the delivery of therapeutically effective doses of the active agent 22 to targeted cells for the treatment of specific disorders. The bioconjugate device 30 can be made by functionalizing crosslinked biopolymer nanoparticles 10, loading an active agent 22 within the colloidal polymer hydrogel. Optionally, the surface of the crosslinked biopolymer nanoparticles 10 can also be functionalized by attaching the targeting molecule 18. The targeting molecule 18 can be any antibody, ligand, signal sequence or molecule that attaches to a functionalized biopolymer 12, for example within the shell 16, and that is capable of increasing the bioconjugate device 30 interaction with specified target cells. The term interaction refers to target cell surface receptor—targeting molecule 18 recognition and bonding, or other indirect mechanisms, whereby the presence of the targeting molecule 18 increases the likelihood of a bioconguate device 30 in the systemic circulation to target, interact with and ultimately transport into a target cell. Fluorescence studies indicate that the crosslinked biopolymer nanoparticles 10 can be taken into the cell nucleus. Without intending to be limited by theory, the transport mechanism is believed to be endocytosis, which may be receptor mediated, or not. Optionally, the degree of crosslinking of the crosslinked biopolymer nanoparticle 10 can be varied to provide a desired release rate of the active agent 22 from the core 14.

In one example, the targeting molecule 18 is an aptamer that typically has a size of less than about 10 nm and increases the diameter of the bioconjugate device 30 by only about 20 nm or less. The aptamer is capable of binding to a target molecule that is located in a specific site which may include cancer cells. For example, AS1411 is an aptamer that has been shown to bind to nucleolin (Soundararajan et al., "Plasma Membrane Nucleolin Is a Receptor for the Anticancer Aptamer AS1411 in MV4-11 Leukemia Cells", Molecular Pharmacology, Vol. 76, No. 5, 2009). Binding to nucleolin receptors is useful in the treatment of a wide array of cancers such as renal cell carcinoma, breast cancer, prostate cancer and others. AS1411 may also be tagged with, for example, a Cy3 fluorescent tag for imaging purposes.

Another potentially useful targeting molecule 18 is the aptamer sgc4. This aptamer was developed by way of the SELEX process from T-cell leukemia cell lines and is able to recognize leukemia cells (Shannguan et al., "Aptamers Evolved from Cultured Cancer Cells Reveal Molecular Differences of Cancer Cells in Patient Samples", *Clinical Chemistry* 53, No. 6, 2007). However, sgc4 has a short biological life if it is not conjugated. Its sequence is described in US Patent Publication 2009/0117549. Shorter variants of the sequence may also be effective. Sgc8c aptamers have also been reported to be useful for targeting leukemia cells (Ozalp et al., *Pharmaceuticals* 2011, 4, 1137-1157)

Targeting molecules, such as aptamers, with an amine modification on the 3' end of the DNA can be linked or attached, for example by one or more covalent bonds, to the carboxyl groups of the functionalized biopolymers 12. The linkage may be made, for example, using EDC chemistry, or by another linkage between the carboxyl and the amine. An example of such a linking using an amine modified test strand of DNA is described in Example 4. Similarly, aptamers such as AS1411 and sgc4 can also be provided with an amine modification and are expected to also attach to functionalized biopolymers 12. When also loaded with an active agent 22, such as doxorubicin, the resulting 22 bioconjugate device 30 may deliver therapeutically effective amounts of the active agent 22 to targeted leukemia cells, or other cancer cells.

By using an immobilized TEMPO as the catalyst to oxidize the biopolymer 12 forms carboxyl groups in the shell 14. These carboxyl groups may be activated by NHS and EDC to attach an amine-modified targeting molecule 18, such as an aptamer, to the surface of the polymer colloid, thereby forming a covalent linkage. The number of functional groups on the surface of the nanoparticle may determine the aptamer surface density and, ultimately, the rate of target cell uptake.

TEMPO reacts with the hydroxyl groups on the starch polymers in an aqueous medium to create the desired carboxyl groups (—COOH) by the process known as TEMPO-mediated carboxylation. NaBr is used to stabilize this reaction. Hypochlorite (NaClO) initiates the reaction by keeping the pH at 10.2-10.5. Then HCl can be used to lower the pH and reprotonate the carboxyl groups. 1-Ethyl-3-(3-dimethylaminopropyl) carbodiimide hydrochloride (EDC) and N-hydroxysuccinimide (NHS) are chemicals which can act as coupling agents to form carboxyl-amino covalent linkages, which link the functionalized biopolymers 12 to the 3'-amine-modified ssDNA aptamer. In this manner, a bioconguate device 30 can be loaded with an active agent 22 and provided with a targeting molecule 18 to increase the interaction of the bioconjugate device 30 with target cells.

Optionally, other molecules can be attached to the cross-linked biopolymer nanoparticle 10, through functional groups or other modifications. For example, PEG or other passivating polymer molecules can be attached to improve the half-life and possibly the bioavailability of the cross-linked biopolymer nanoparticles 10 and the bioconjugate devices 30 based thereupon.

The following examples serve to illustrate one or more parts of one or more inventions and are not intended to limit any claim. Reference is made in the examples to Eco-Sphere® 2202 from EcoSynthetix Inc. as a non-limiting example of a crosslinked biopolymer nanoparticles 10. However, other nanoparticles with similar properties of drug loading, functionalization, target molecule attachment and variable degrees of crosslinking are also contemplated.

Example 1

Incorporation of Fluorescent Agents into Starch Based Nanoparticles

Incorporation of two compounds, in particular the fluorescent model compound Calcein and the fluorescent anticancer agent doxorubicin (IUPAC Name: (7S,9S)-7-[(2R, 4S,5S,6S)-4-ami no-5-hydroxy-6-methyloxan-2-yl]oxy-6,9, 11-trihydroxy-9-(2-hydroxyacetyl)-4-methoxy-8,10-dihydro-7H-tetracene-5,12-dione; commercial products include Adriamycin™ and Doxil™), into crosslinked biopolymer nanoparticles 10 (EcoSphere® 2202 from EcoSynthetix Inc.) was accomplished by a phase separation technique. This technique involves the formation of a water-in-oil emulsion. In a 250 mL round bottom flask, the starch based nanoparticles were dispersed at <5% solids (w/w) in water under mechanical agitation at a pH of about 10 using dilute caustic. The resultant dispersion was titrated to a pH of 7 using dilute hydrochloric acid. The substance to be incorporated in the crosslinked biopolymer nanoparticle colloid matrix (calcein or doxorubicin) was dissolved in the dispersion containing the biopolymer nanoparticles. The amount of encapsulated active agent 22 prepared ranged from 0.04%-0.4% (w/w). The flask was placed inside an insulated container and secured properly. The solution was then stirred for several minutes. Hexane was added drop wise under continuous agitation until an emulsion was formed. The emulsion was immediately frozen using liquid nitrogen. The flask was connected to a vacuum system and lyophilization was carried out at −85° C. After 24 hours, when the vacuum gauge indicated no further vapor removal, the dried sample was removed from the vacuum system and stored at −10° C.

Example 2

Drug Release Studies

Figure 8:
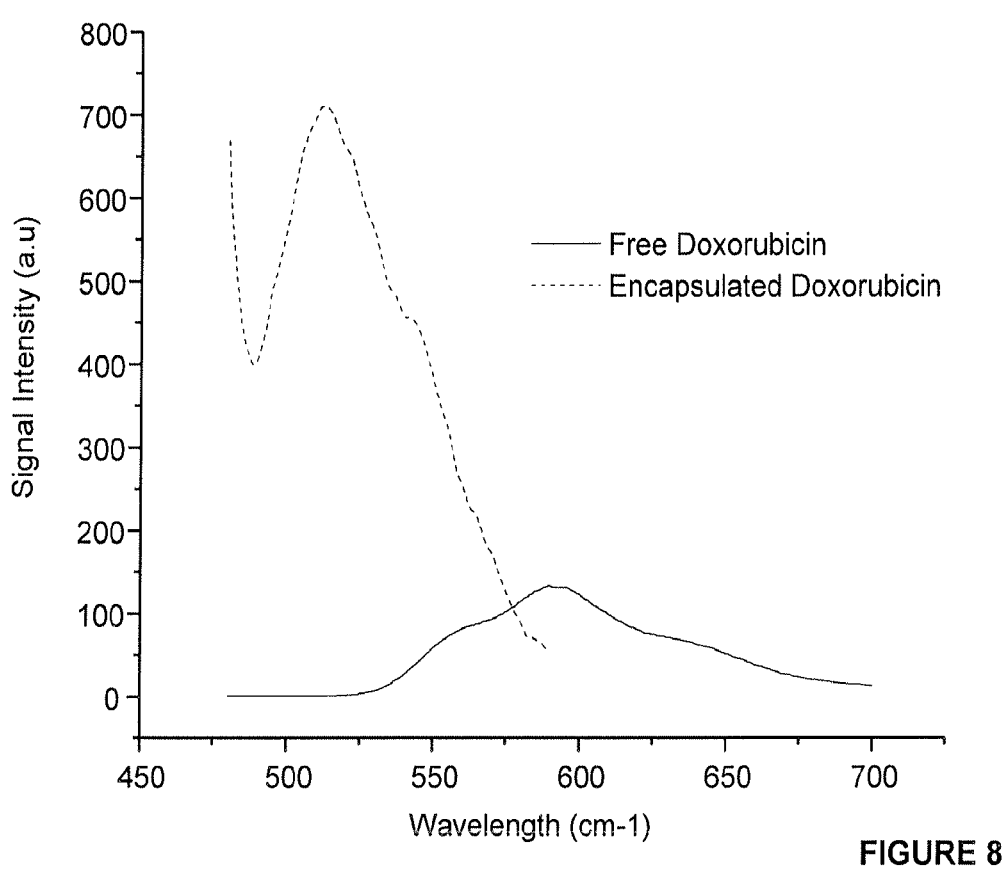
FIG. 8 is a chart showing the fluorescence spectrum of free doxorubicin and doxorubicin entrapped in the example crosslinked biopolymer nanoparticles of FIG. 2B.
Figure 9A:
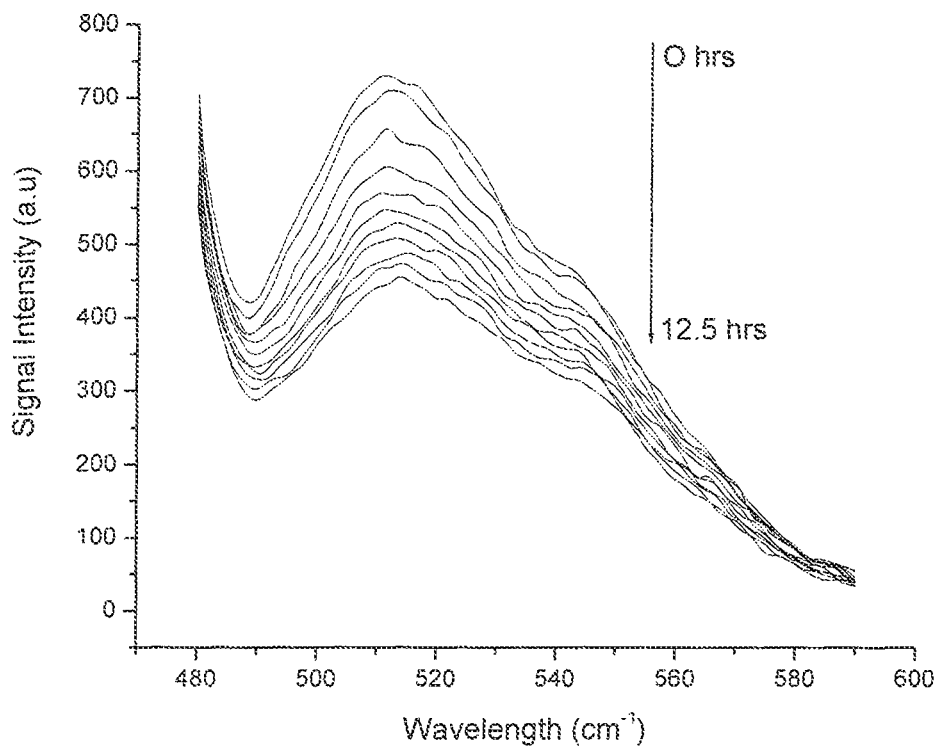
FIG. 9 is a chart showing a release profile of doxorubicin from the example crosslinked starch nanoparticles of FIG. 2B.
Figure 10A:
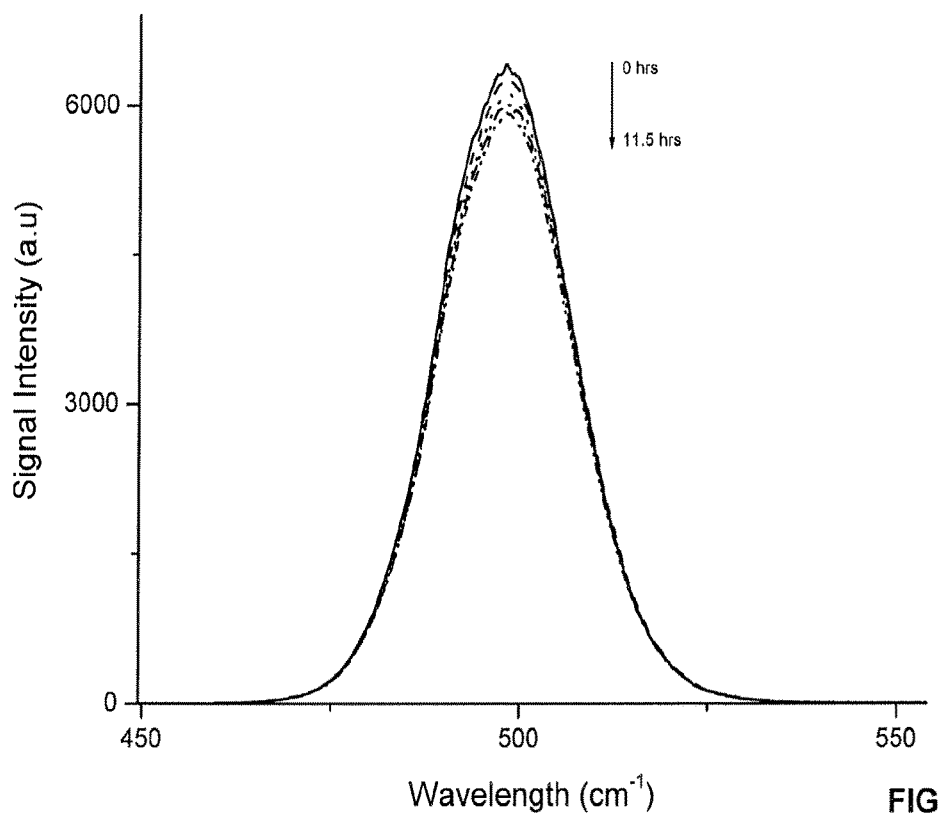
FIG. 10 is a chart showing the fluorescence spectrum of Calcein and a release profile of Calcein from the crosslinked biopolymer nanoparticles of FIG. 2B.

The use of fluorescent dyes as spectral probes to investigate inclusion complexation is known (see Saenger, W. Angew. Chem. 1980, 92, 343-61 and Wenz, G. Angew. Chem. 1994, 106, 851-70). This approach was adopted in studying the efficacy of starch based nanoparticles (in this example we used EcoSphere® 2202 from EcoSynthetix Inc.) to encapsulate selected drugs and the ability of this material to release the drug over time. Fluorescent compounds such as calcein and doxorubicin are very sensitive to environmental changes. The fluorescent signal of the molecules was enhanced when it was incorporated into the matrix of starch based nanoparticles. As shown in FIG. 8, the signal intensity of free doxorubicin is much lower than that of the encapsulated doxorubicin. In addition, a significant hypochromic shift (change of spectral band position in the emission spectrum of a molecule to a shorter wavelength) is observed when doxorubicin is encapsulated. FIG. 9A shows a series of fluorescence spectra of doxorubicin obtained as a function of time. It can be seen that there is a significant decrease in signal intensity with time, indicating sustained release of the active agent 22. In addition, there was a relatively small bathochromic shift (change of spectral band position in the emission spectrum of a molecule to a shorter wavelength) observed. Without intending to be limited to any theory of operation, it appears that the reduced shift indicates a biphasic release mechanism given that not all of the active agent 22 was released over the course of the 12 hour experiment. FIG. 10A shows a series of fluorescence spectra of calcein obtained as a function of time. It can be seen that there is a decrease in signal intensity with time, indicating sustained release of the active agent 22.

Figure 9B:
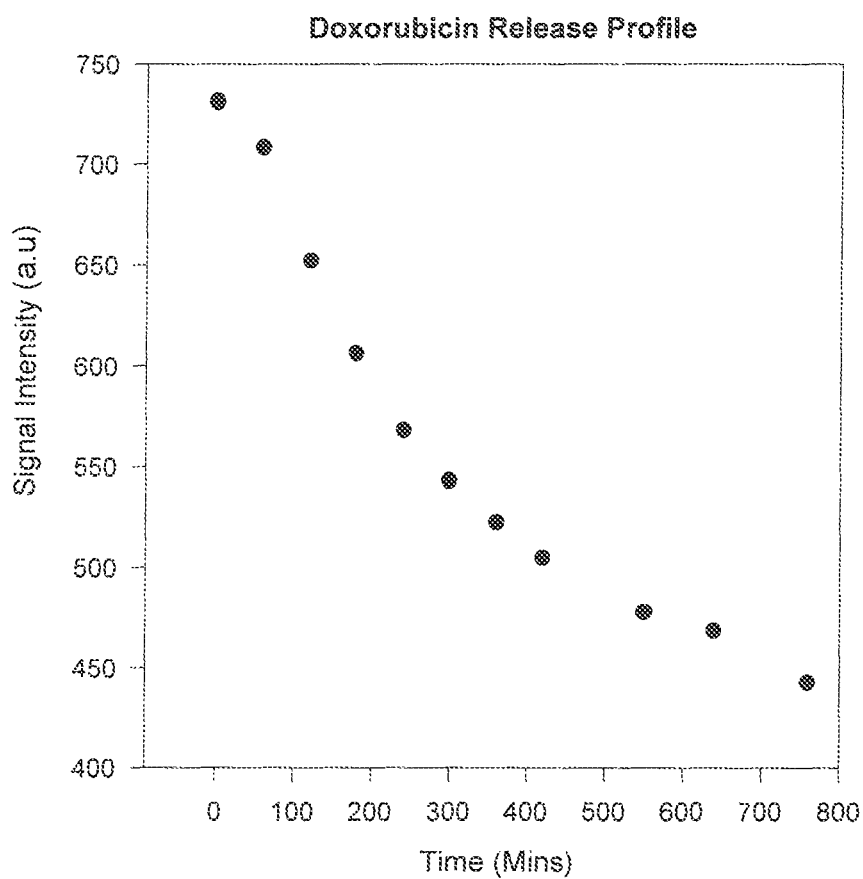
Figure 10B:
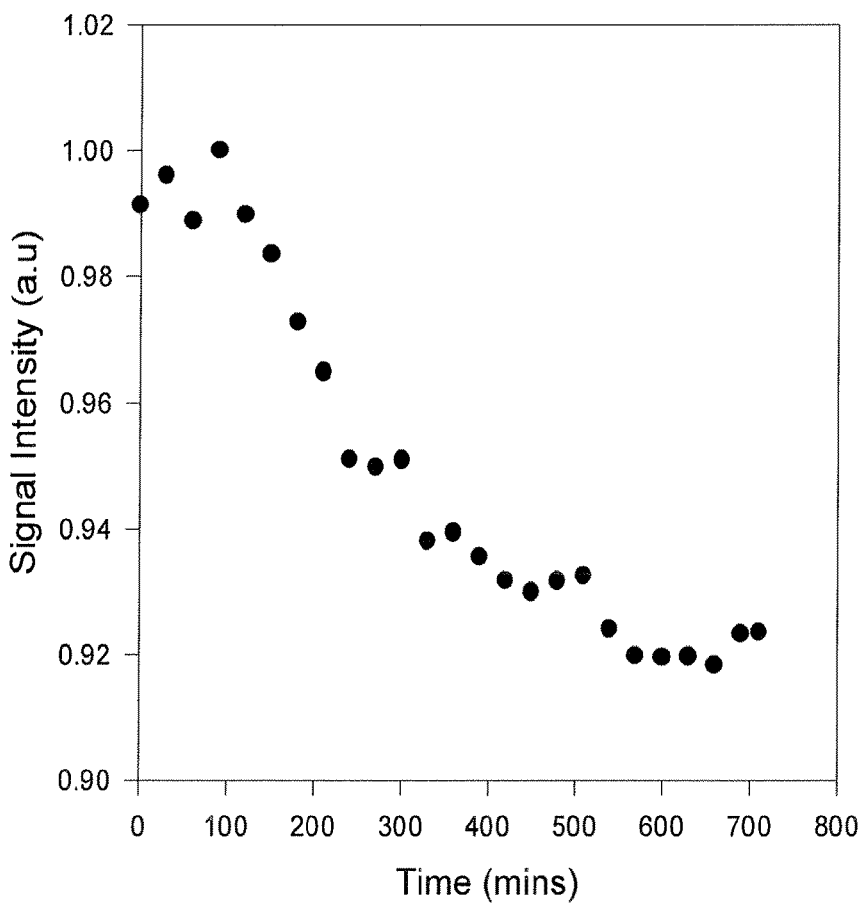

The data shown in FIGS. 9A and 10A illustrate that enhancement in signal intensity for calcein and doxorubicin due to inclusion complexation with the starch based nanoparticles can be used to monitor the release of the active agent. FIGS. 9B and 10B are plots of signal intensity as a function of time at the maximum signal intensity of the fluorescence emission spectra for doxorubicin and calcein, respectively. These data show that the concentration of fluorophore molecules inside the supramolecular cavity is changing with time. The release of the molecules appears to be proportional to the concentration gradient of the active agent. The sustained release of active agent from the biopolymer nanoparticles extended to more than 10 hours. The results demonstrate that the biopolymer nanoparticles provide a stable matrix for the steady release of active agent over an extended time period. The release mechanism appears to be predominantly diffusion controlled.

Example 3

In Vivo Studies of Human Xenographs Implanted in Athymic Mice

In order to demonstrate the efficacy of the crosslinked biopolymer nanoparticles 10 as a drug delivery device, they were loaded with the anticancer drug doxorubicin as described in Example 1. The doxorubicin loaded in crosslinked biopolymer nanoparticles 10 was administered to athymic mice which had a human xenograph of a primary brain tumor (D 245 glioblastoma multiform) previously grown at a subcutaneous site. Athymic mice were chosen for these studies because normal mice are capable of immunologically rejecting implanted foreign xenographs, specifically human tumors. The animals (both control and treated) were monitored for tumor regression and survival. The results of the study are presented in Table 1.

The procedure consisted of inoculation of the tumor xenograph into a subcutaneous site in athymic mice. The subcutaneous tumors were grown to approximately 200 cubic millimeters in size (6-8 mm in diameter). Subsequently, either the free drug or the drug loaded nanoparticles were injected at the tumor site or i.p. (intra peritoneal). Typically it took approximately 20 days for the animals to test out. The animals were treated in groups of 8 to 10 individuals. The highest survival rates (highest T-C values or increased life span in days) occurred in individuals in which several doses of doxorubicin loaded nanoparticles were administered. Table 1 demonstrates the efficacy as well as the safety of the doxorubicin loaded biopolymer nanoparticles in treating a primary human brain tumor in athymic mice.

facilitate the interaction of the delivery system with a tumor, metastatic cancer cell, or other targeting tissue or organ. This capability was demonstrated by the following procedures and tests.

Oxidation of Crosslinked Biopolymer Nanoparticles

Various different types of functionalities may be introduced onto the crosslinked biopolymer nanoparticles 10 to provide binding sites for the aptamer as well as the active agent 22. As described above, various chemical modification techniques can be employed. A particularly useful chemical modification is oxidation of starch biopolymers 12 to produce carboxyl functionalities. To illustrate this, TEMPO-mediated oxidation was carried out for both crosslinked biopolymer nanoparticles 10 (EcoSphere® 2202 from Eco-Synthetix Inc.) as well as for regular native (unmodified) corn starch. In this method, the starch biopolymer 12 was oxidized with sodium hypochlorite (NaClO) and 2,2,6,6-tetramethylpiperidin-1-oxyl (TEMPO) radicals, at temperatures between 0 and 4° C. and pH of 10.8. The degree of oxidation was controlled by amount of NaClO added. As noted, two types of starch were used. The first was EcoSphere® starch based nanoparticles and the second one was

TABLE 1

In vivo studies of human xenographs implanted in athymic mice

| | Dose × Conc. (w/w) | | | | | | | |
|---|---|---|---|---|---|---|---|---|
| | 1 × 0.03% (Dox-nano) | 1 × 0.5% (Dox-nano) | 1 × 0.5% (Dox-nano) | 2 × 0.5% (Dox-nano) | 4 × 0.5% (Dox-nano) | 4 × 0.5% (Dox-nano) | 1 × 2% (Dox-nano) | Free Dox Control |
| Drug dose | 0.075 mg/kg | 1.25 mg/kg | 1.25 mg/kg | 2.5 mg/kg | 5 mg/kg | 5 mg/kg | 5 mg/kg | 5 mg/kg |
| T − C(days) | 0.99 | 4.8 | 5.31 | 8.09 | 7.56 | 6.57 | 2.44 | 1.53 |
| P value | 0.14 | 0.14 | 0.14 | 0.04 | 0.001 | 0.012 | 0.03 | 0.32 |
| Regressions | 2/8 | 2/8 | 0/10 | 0/10 | 2/9 | 0/9 | 2/8 | 0/10 |
| Toxic deaths | 0/8 | 0/8 | 0/10 | 0/10 | 2/9 | 0/9 | 0/8 | 0/10 |

The following abbreviations are used in Table 1: "Dox"=doxorubicin; "Dox-nano"=doxorubicin loaded crosslinked biopolymer nanoparticles 10.

Dispersions were 100 mg crosslinked biopolymer nanoparticles/5 mL saline (1×0.5% Dox-nano), 200 mg crosslinked biopolymer nanoparticles/5 mL saline (2×0.5% Dox-nano) or 400 mg crosslinked biopolymer nanoparticles/5 mL saline (4×0.5% Dox-nano).

Injections were each 0.25 mL/20 gram mouse (all single injections).

T-C is defined as: Average of (days lived by drug-treated animal minus days lived by control animals); i.e., increased life span in days.

The Control was provided as follows: Varied—Untreated mice injected with saline; Untreated mice; Mice treated with drug-free crosslinked biopolymer nanoparticles (100 mgs/5 mL saline).

P value: Test run for significance. P values are calculated using non-parametric statistical method by Hollander and Wolfe.

Regressions: Indicate that tumors drop below previous measurement and stay below for 2 consecutive measurements.

Example 4

Attaching a Targeting Molecule

Targeting molecules can be attached to the crosslinked biopolymer nanoparticle bioconjugate delivery system to regular corn starch purchased from Sigma-Aldrich. The procedures were as described below.

In a glass jar, 4 g of EcoSphere® and 80 mL MilliQ water were added and mixed thoroughly to create a ~5% dispersion. In a second jar 4 g of Corn Starch and 80 mL of MilliQ water were added to create a ~5% solution. The second jar was heated up to above 80° C. (max 95° C.) under agitation and allowed to fully dissolve. Subsequently it was cooled to room temperature. Separately, in two 45 mL tubes 40 mL of water, 38 mg TEMPO, and 508 mg NaBr were added into each tube (0.01 mol TEMPO per anhydroglucose unit of starch; 0.2 mol NaBr per anhydroglucose unit of starch), stirred until fully dissolved, and cooled for 30 minutes in an ice batch. Next the content of one tube was mixed into each jar. A pH measurement was taken, which initially was 3.8 for the EcoSphere® jar and 7.4 for the Corn Starch jar. Next 450 µL of 0.5 M NaOH was added to the EcoSphere® jar to reach pH 10.75, and 200 µL of 0.5 M NaOH was added to the Corn Starch jar to reach pH 10.75. Subsequently, 10 mL of NaClO was added when the pH dropped to around 6-7, and pH measurements were taken every 10-15 min. As the mixtures continued to stir and the pH dropped, the color became darker (yellow/orange). A total of 60 mL NaClO was added and the pH was finally adjusted to 8.0 before the oxidized starch was diluted 1:1 with ethanol. Ethanol precipitated the modified EcoSphere® nanoparticles and modified starch and they were harvested by centrifugation and washed by water and ethanol and finally dried by lyophilization (freeze-drying).

The oxidized EcoSphere® was characterized by zeta-potential measure and dynamic light scattering. Zeta measurement showed that the modified particles carried a negative charge with zeta-potential of −25.5 mV, while unmodified particles were essentially neutral. The size of the particles appeared to be slightly smaller compared to the non-oxidized ones (i.e. the NTA Mode was 113 versus 141 nm).

The color of the final product depended on the pH of the solution after oxidization. If the pH was too high (higher than 10), a yellow colored product was obtained. It was found that this color can be removed by lowering the pH.

DNA Attachment

Subsequently, amino-modified and fluorescently labeled DNA was attached to the starch nanoparticles using N-(3-Dimethylaminopropyl)-N'-ethylcarbodiimide hydrochloride (EDC) as a coupling agent. The reaction mixture contained 5 µM FAM (6-carboxyfluorescein) and amino dual labeled DNA, 1-5% COOH-modified starch, 20 mM 2-(N-morpholino)ethanesulfonic acid (MES) buffer, pH 6.0 and 20 mM freshly prepared EDC was added the last. Agarose gel electrophoresis was carried out for DNA and DNA-conjugated to TEMPO-oxidized EcoSphere® nanoparticles. It was found that the gel fluorescence intensity was more evenly distributed and some of the DNA migrated more slowly, indicating conjugation to the starch nanoparticles. In some of the alternative DNA attachment protocols the carboxyl groups on starch were first activated using N-Hydroxylsuccinimide (NHS) at 5 mM (¼ of the amount of EDC) for 15 minutes before adding the DNA. Next this mixture was allowed to react for several hours. Without intending to be bound by any particular theory of operation, NHS may help to facilitate the EDC linking reaction by activating carboxyl groups so it can react with an amine to form an amide, rather than a salt with an amine.

Thus the DNA used in this example, which served as a model compound for ligand attachment, was successfully attached. The DNA sequence was 5'-FAM-ACG CAT CTG TGA AGA GAA CCT GGG-NH$_2$-3'.

Attachment of an Aptamer

An aptamer was attached to EcoSphere® 2202 particles using the procedure described above. Attachment of the aptamer was confirmed by laboratory observations of nanoparticle fluorescence. The aptamer was, AS1411, which is believed to have (as modified) the sequence: 5-Cy3-TTGGTGGTGGTGGTTGTGGTGGTGGTGG-NH$_2$-3' (i.e. AS1411 aptamer with Cy3 fluorescent tag and amine group). The fluorescent tag, used for imaging purposes in the diagnostic gel electrophoresis test, can of course be omitted if needed. However, an additional purpose for the fluorescent tagging is to facilitate monitoring of the binding and uptake of the modified nanoparticles by a cell. As for the DNA described above, the aptamers had an amine modification on the 3' end of the DNA so that it could be linked using EDC chemistry to carboxyl functionalities on the nanoparticle.

Four 200 microliter wells were prepared with cells of a cervical cancer cell line (HeLa) and given time to culture and grow. Well 1 was left with only the HeLa cells. Well 2 had unconjugated AS1411 added to it. Well 3 had EcoSphere® 2202 nanoparticles with conjugated AS1411 added to it. Well 4 had nanoparticles conjugated with a control sequence added to it. The control sequence has no known affinity for HeLa cells. The wells were then allowed to culture for a further 48 hours.

After the 48 hours had elapsed, cells from the wells were washed to remove any fluorescent marks on any unbound particles external top the cells. The cells were then observed under a fluorescence microscope. Fluorescent marks were observed within the cells of well 3 confirming that the nanoparticle/aptamer conjugate had been taken into the cells.

Drug Adsorption and Release Studies

In a dilute aqueous dispersion (e.g. 1-5%) the EcoSphere® nanoparticles are highly swollen and their density is close to that of water. As a result, centrifugation and even ultracentrifugation were ineffective methods to separate the particles from the aqueous dispersion media. Instead, drug loading was evaluated by way of fluorescence change. It was found that the adsorption of the anticancer drug doxorubicin (Dox) was very much improved after modification of the EcoSphere® nanoparticles with carboxylate groups. Upon adsorption, the fluorescence of doxorubicin was also quenched by the carboxylated EcoSphere®. This was clearly visible under the 245 nm excitation in a dark room using a handheld UV lamp. The fluorescence quenching provides an analytical method to monitor doxorubicin adsorption.

To ensure that the observed quenching was not due to a pH effect, the fluorescence was subsequently compared for the following: doxorubicin was dissolved at a final concentration of 0.01 mg/mL in unmodified EcoSphere®, COOH-modified EcoSphere® and buffer (no EcoSphere®). For each condition, two pH conditions were tested to contain either 20 mM sodium acetate buffer (pH 5.0) or 20 mM 4-(2-hydroxyethyl)-1-piperazineethanesulfonic acid (HEPES) buffer, pH 7.6. The final pH was confirmed to be at the intended values.

Free doxorubicin fluorescence was strong in both pH 5 and 7.6 in water. Mixing with 1% unmodified EcoSphere® nanoparticle dispersion induced about 50% fluorescence quenching but mixing with a COOH-modified EcoSphere® nanoparticle dispersion completely quenched the fluorescence. This confirmed that COOH-modified EcoSphere® is better at adsorbing doxorubicin. Without intending to be bound by any particular theory of operation, this is likely due to electrostatic interactions with the positively charged doxorubicin. Therefore, tuning the EcoSphere® charge will allow selective adsorption of various drugs and in addition provide a way of controlling the release profile.

Electrokinetic Measurements

To evaluate the presence of electrostatic charges on the surface of the particles, the zeta potential of the biopolymer nanoparticles and TEMPO oxidized biopolymer nanoparticles was determined from the analysis of the electrokinetic measurements using a Brookhaven ZetaPlus instrument. The crosslinked starch particles were suspended in a solution of NaCl ranging from 0.001 M to 0.1 M concentration, and their electrophoretic mobilities were determined. The electrophoretic mobilities were converted to zeta ($\zeta$) potentials using the Smoluchowski expression, which assumes small particles and dilute ion concentration. The zeta potential of the un-modified starch based nanoparticles was determined to be close to zero, whereas the zeta potential of the TEMPO modified biopolymer nanoparticles was determined to be −25 mV which indicates negatively charged nanoparticles.

Particle Size Analysis

The particle size of dispersed starch based nanoparticles and the TEMPO modified nanoparticles was determined by Nanoparticle Tracking Analysis (NTA) using an LM 20 tracking analysis device (NanoSight Ltd.) equipped with a blue laser (405 nm). The device uses a 50 mW laser operating in the CW mode to illuminate the particles. The light scattered by the particles is captured using a digital camera and the motion of each particle is tracked from frame to frame using NanoSight software. A high speed video is obtained (30 frames per second, average video about 30 s). The trajectories of individual particles are generated from the video sequence and the mean squared displacement determined for each particle. Typically at least 20 trajectories are acquired and 250 to 500 sets of trajectories (each set corresponding to an individual particle) are accumulated in a video sequence. The analysis of the mean squared displacement is used to calculate the diffusion coefficient and the hydrodynamic radius ($r_h$) is determined using the Stokes-Einstein equation. Thus, the diameter of each particle in the sample can be determined and a true particle size distribution derived. Because a diffusion coefficient is obtained for each particle in the field of view, a particle size distribution can be obtained which does not assume a particular mathematical model as in dynamic laser light scattering (DLS) analysis.

Dispersions of biopolymer nanoparticles were prepared using the following procedure: 1) dry agglomerate EcoSphere® powder was mixed in water containing 0.4 wt % sodium carbonate ("lite soda ash") based on dry weight in a Silverson high shear mixer for 15 minutes; the final concentration of the dispersed biolatex ranged from 0.015 to 0.030% (w/w); 2) this dispersion was heated to 45° C. for 15 minutes in a water bath prior to measurement to ensure the agglomerate particles were fully dispersed into nanoparticles.

Example 5

Three batches of crosslinked biopolymer nanoparticles 10 with different degrees of crosslinking were made. A first batch 100 had the lowest amount of crosslinking, a second batch 102 had a moderate amount of crosslinking and a third batch 104 had the highest degree of crosslinking. One manner to assess the degree of crosslinking is to determine the maximum volume swell ratios, also referred to as the effective volume factor, as described in Do Ik Lee, Steven Bloembergen, and John van Leeuwen, "Development of New Biobased Emulsion Binders", PaperCon2010, "Talent, Technology and Transformation", Atlanta, Ga., May 2-5, 2010, the disclosure of which is incorporated herein by reference. Briefly, crosslinked biopolymer nanoparticles swell under conditions of extreme dilution with water to achieve the maximum swelling value that is balanced between their elastic constraint due to their crosslinked network and the osmotic pressure (see Bloembergen, S., McLennan, I., Lee, D. I., and van Leeuwen, J., "Paper Binder Performance with Nanoparticle Biolatex™: EcoSynthetix develops EcoSphere® biolatex for replacement of petroleum based latex binders", ACFS, Montreal, Jun. 11-13, 2008).

By measuring the relative viscosity, $\eta_r$, at low concentrations (i.e. low volume fraction) for a latex (a polymer colloid), one can gather relevant information about the viscosity and swelling behavior of that colloid. The relative viscosity ($\eta_r = \eta/\eta_o$) of a biobased latex binder is obtained by simply measuring the flow times between two demarcations of a glass Ubbelohde viscometer for the biobased latex dispersion ($\eta$) and for its dispersion medium ($\eta_o$), which is water. Using the Einstein equation, $\eta_r = 1 + 2.5$ f $\varphi$, where f is the effective volume factor and $\varphi$ is the volume fraction, one can obtain the effective volume factor (f) that is equal to the maximum volume swelling of biobased latex nanoparticles at very low concentrations. The first batch 100 had a maximum volume swell ratio of 16.0, the second batch 102 had a maximum volume swell ratio of 9.33 and the third batch 104 had a maximum volume swell ratio of 6.67.

The three batches 100, 102, 104 were loaded with 5% doxorubicin by mass, as described above, and dispersed in 5 mL of Milli-Q water. The released doxorubicin was separated from the crosslinked biopolymer nanoparticles 10 using dialysis with a molecular weight cut off of 25 kDa. Samples were drawn off at various times over 72 hours and the fluorescence was measured using a fluorescence plate reader.

As shown in FIG. 12, the initial background was close to zero, suggesting that little free doxorubicin was present and the loading capacity of the three batches 100, 102, 104 was high. The first batch 100 demonstrated the fastest rate of doxorubicin release. The third batch 104 released approximately 20% of the drug after 3 days while the first batch 100 released more than 50% of the doxorubicin over the same period. Without being bound by theory, these results indicate that the level of crosslinking may be used to control the release profile of the active agent 22 from the core 14 of the bioconjugate device 30.

Example 6

The degree, or effect, of multivalent binding between the targeting molecule 18 and the target cell surface receptors may modulate the transport of the bioconjugate device 30 into the phospholipid membrane of the target cell. Samples were prepared with different ratios of functionalized, crosslinked biopolymer nanoparticles 10 relative to the targeting molecule 18, in this example the AS1411 aptamer was attached similar to the approach described above. The concentration of functionalized crosslinked biopolymer nanoparticles 10 is represented by (glycosidic) repeating units of glucose. The inventors prepared samples with the following molar ratios of glucose repeating units to aptamer: 100:1; 500:1; 1000:1; and 5000:1. These samples, free (unattached) aptamer and a control DNA aptamer were incubated with HeLa cells for 2 hrs. The HeLa cells were seeded and cultured in a $CO_2$ incubator with 5% oxygen in an eight-well slide for two days to achieve a confluence of ~70%. The culture media was DMEM/F-K12 1:1 (Hyclone) with 10% fetal bovine serum and 1% penicillin and streptomycin. In pairs of wells, we added to each 20 μL of 10 μM unconjugated AS1411 aptamer, 10 μM unconjugated control DNA aptamer or 20 μL of 3 mg/mL conjugated SNPs. These were incubated for a further 2 hours at 37° C. and 5% $CO_2$. The unbound materials were washed away with phosphate buffered saline (PBS, from Cellgro).

Figure 13:
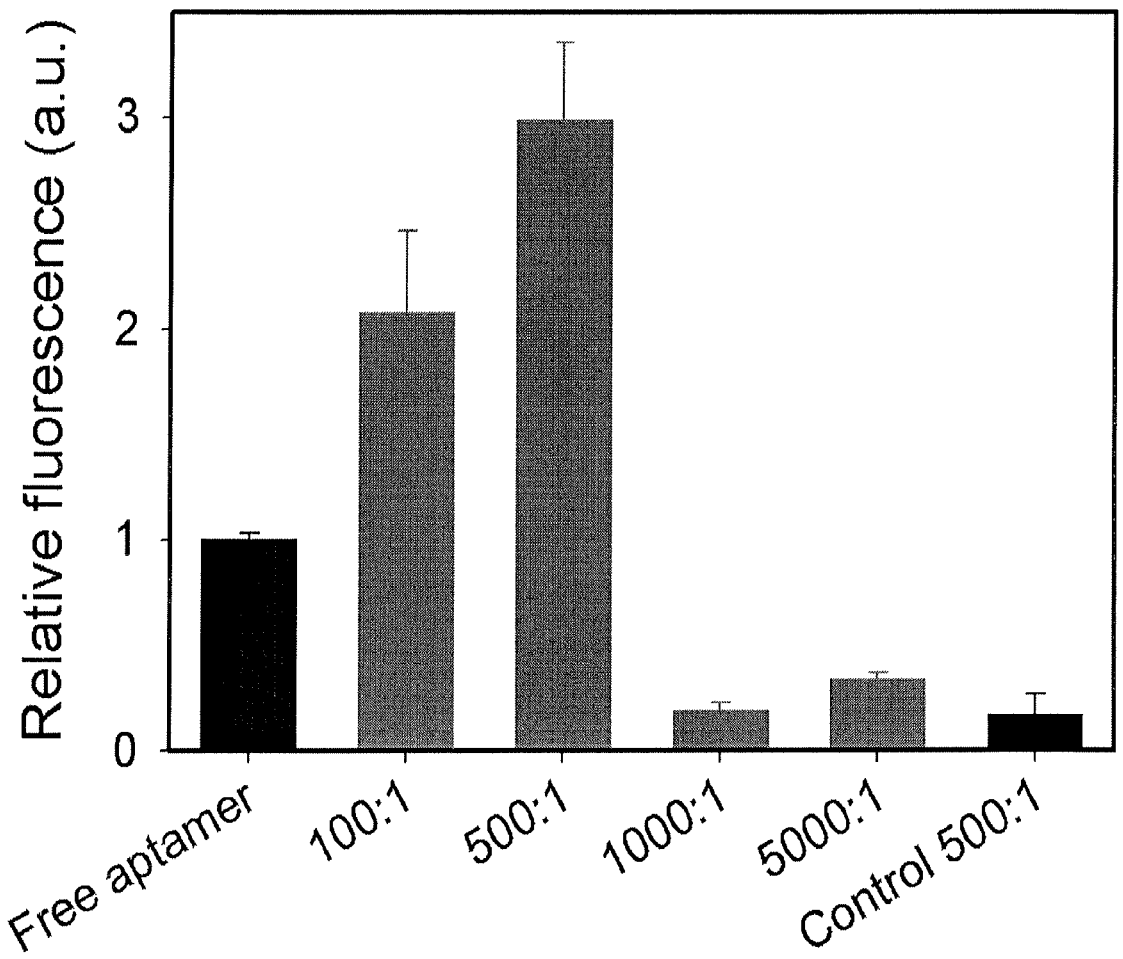
FIG. 13 is a chart that shows the uptake of crosslinked biopolymer nanoparticles with varying levels of attached aptamer, where the captions mean as follows: "Free aptamer" is the fluorescence result for cellular binding or uptake of the unconjugated AS1411 aptamer; "100:1", "500:1", "1000:1" and "5000:1" is the fluorescence result for cellular binding or uptake of crosslinked bioconjugates formulated with relative ratios of 100, 500, 1000, and 5000 parts of glucose repeating units in the biopolymer to one part AS1411 aptamer; and "Control 500:1" is the fluorescence result for cellular binding or uptake of a bioconjugate formulated with 500 parts of glucose repeating units in the biopolymer to one part of a control aptamer sequence which is untargeted to cancer cells.

The control DNA aptamer was attached in a ratio of 500:1 (glucose:control aptamer) and the control DNA aptamer is not targeted to recognize or interact with surface features of cancer cells. After washing the cells to remove unbound and free material, uptake was quantified using a fluorescence microplate reader. The fluorescence was normalized to the equivalent dose of free aptamer. As depicted in FIG. 13, the 500:1 sample demonstrated the highest uptake. It is likely that at ratios at or beyond 1000:1, or possibly beyond about 750:1, the distance between aptamers was too far to impart a significant multivalent binding effect. If the aptamers are packed too closely, proper folding and interaction, for example binding between the bioconjugate device 30 and the cells, may have been hindered.

Example 7

Figure 14:
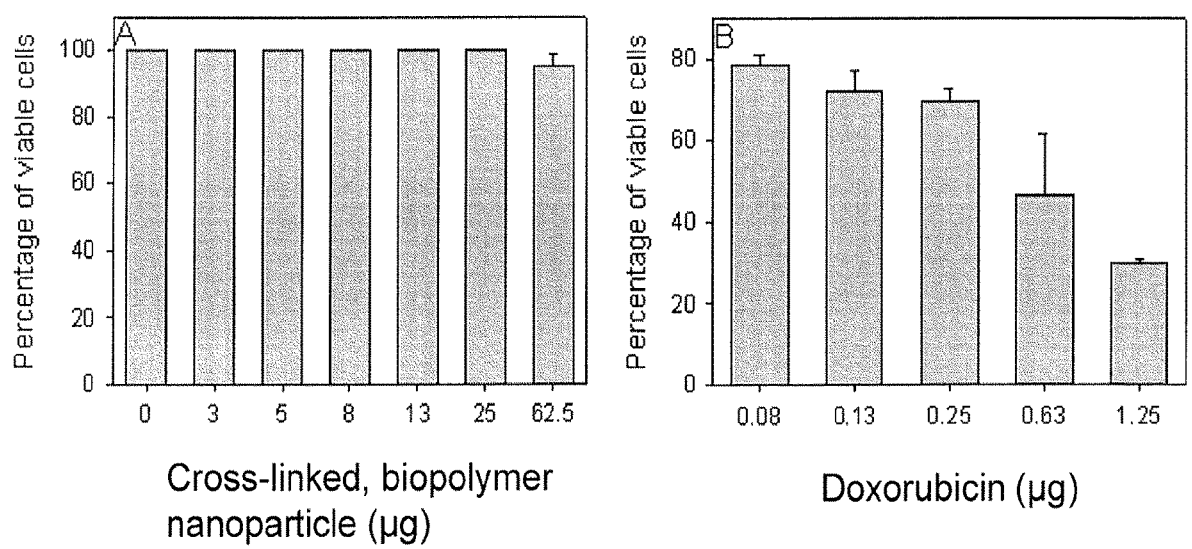
FIGS. 14A and 14B are charts that show the viability of cells treated with crosslinked biopolymer nanoparticles with and without a loaded active agent.

HeLa cells, cultured as described above, were exposed for 24 hours to different bioconjugate devices 30 to assess cell viability. Cell viability was measured with a lactose dehydrogenase (LDH) assay and the fluorescence was measured at 490 nm using a microplate reader. Unmodified, crosslinked biopolymer nanoparticles 10 without any loaded active agent 22 were non-toxic to cells over a range of doses (FIG. 14A). Bioconjugate devices 30, with the AS1411 attached aptamer, were loaded 5% by mass with doxorubicin. Different doses of these bioconjugate devices were given to the cells, and there was increased cell killing with doxorubicin levels greater than 0.625 µg. Under similar experimental conditions, 0.625 µg of free doxorubicin (not shown) was less effective at killing the cells (83% viability, p=9.0 E−4) than 12.5 µg of loaded bioconjugate device 30 that delivered a total of 0.625 µg of doxorubicin. Further, the bioconjugate device 30, with the AS1411 aptamer attached, and no doxorubicin was non-toxic to the cells (not shown). Without being bound by theory, the inventors attribute these results to the ability of the bioconjugate device 30 to penetrate the cell membrane and release the doxorubicin inside of the cells, which is compared to the passive penetration of the cell membrane by free doxorubicin.

The above description and attached figures are intended to illustrate at least one embodiment of each claim and not to limit any invention. The invention is defined by the following claims.

We claim:
1. A delivery system comprising
   nanoparticles comprising a mass of crosslinked and functionalized starch biopolymers, wherein the starch biopolymers comprise glucose repeating units and carboxyl groups; and,
   amine modified aptamer targeting molecules directly linked to the carboxyl groups of the nanoparticles,
   wherein the aptamer targeting molecules are attached to the nanoparticles in an amount sufficient to provide a molar ratio of the glucose repeating units to the targeting molecules within a range from about 100:1 to less than 1000:1.
2. The delivery system of claim 1 wherein the nanoparticles have an average size in the range of 50 to 150 nm when measured by any of nanoparticle tracking analysis or dynamic laser light scattering.
3. The delivery system of claim 1 having a molar ratio of glucose repeating units to targeting molecules within a range from about 100:1 to 750:1.
4. The delivery system of claim 1, further comprising an active agent loaded into the nanoparticles.
5. The delivery system of claim 4, wherein the active agent is a chemotherapeutic drug.
6. The delivery system of claim 5 wherein the drug is selected from the group consisting of doxorubicin ((7S,9S)-7-[(2R,4S,5S,6S)-4-amino-5-hydroxy-6-methyloxan-2-yl]oxy-6,9,11-trihydroxy-9-(2-hydroxyacetyl)-4-methoxy-8,10-dihydro-7H-tetracene-5,12-dione), cyclophosphamide ((RS)-N,N-bis(2-chloroethyl)-1,3,2-oxazaphosphinan-2-amine 2-oxide) and carmustine (N, N'-bis(2-chloroethyl)-N-nitroso-urea).
7. The delivery system of claim 4 wherein the nanoparticles have a swell ratio of between 6.67 and 16 and release 20% to about 55% of the active agent after 3 days of being dispersed in water.
8. The delivery system of claim 1 wherein the aptamer targeting molecules increase the diameter of the nanoparticles by about 20 nm or less.

SEQUENCE LISTING

<160> NUMBER OF SEQ ID NOS: 2

<210> SEQ ID NO 1
<211> LENGTH: 24
<212> TYPE: DNA
<213> ORGANISM: Artificial Sequence
<220> FEATURE:
<223> OTHER INFORMATION: Linker

<400> SEQUENCE: 1
acgcatctgt gaagagaacc tggg                                           24

<210> SEQ ID NO 2
<211> LENGTH: 28
<212> TYPE: DNA
<213> ORGANISM: Artificial Sequence
<220> FEATURE:
<223> OTHER INFORMATION: Aptamer

<400> SEQUENCE: 2
ttggtggtgg tggttgtggt ggtggtgg                                       28

9. The delivery system of claim 1 wherein the molar ratio of glucose repeating units to targeting molecules is within a range between about 100:1 and about 500:1.

10. The delivery system of claim 1 wherein the nanoparticles have a swell ratio of between about 6 and 16.

* * * * *